United States Patent [19]

Kelly et al.

[11] 4,096,324

[45] Jun. 20, 1978

[54] CYTIDINE NUCLEOSIDE COMPOUND

[75] Inventors: Robert C. Kelly; William J. Wechter, both of Kalamazoo, Mich.

[73] Assignee: The Upjohn Company, Kalamazoo, Mich.

[21] Appl. No.: 654,019

[22] Filed: Jan. 30, 1976

Related U.S. Application Data

[60] Division of Ser. No. 593,890, Jul. 7, 1975, abandoned, which is a continuation-in-part of Ser. No. 427,183, Dec. 21, 1973, abandoned, which is a continuation of Ser. No. 11,826, Feb. 16, 1970, Pat. No. 3,847,898, which is a continuation-in-part of Ser. No. 828,380, May 27, 1969, abandoned.

[51] Int. Cl.$^2$ ............................................. C07H 19/08
[52] U.S. Cl. ..................................... 536/23; 424/180; 536/29
[58] Field of Search ............... 424/180; 260/211.5 R; 536/23, 29

[56] References Cited

U.S. PATENT DOCUMENTS

| | | | |
|---|---|---|---|
| 3,462,416 | 8/1969 | Hanze et al. | 260/211.5 R |
| 3,721,664 | 3/1973 | Hoffer | 260/211.5 R |
| 3,894,000 | 7/1975 | Wechter et al. | 260/211.5 R |

*Primary Examiner*—Johnnie R. Brown
*Attorney, Agent, or Firm*—William G. Jameson; Sidney B. Williams, Jr.

[57] ABSTRACT

5'-Esters of ara-cytidine (1-β-D-arabinofuranosylcytosine) are prepared by reacting ara-cytidine with β,β,β-trihaloethoxycarbonyl halide or other protective agency to form a protective amido group on the primary amino nitrogen of ara-cytidine and then reacting the thus-protected compound with a reagent reactive with the 5'-O-hydroxyl group, e.g., an acylating agent, to form the 5'-O-derivative. The β,β,β-trihaloethoxycarbonyl or other protective group is then removed. Alternately, the primary amino group of ara-cytidine can be protected from acylation by protonation. The 5'-O-derivatives in their free base of salt form are characterized in that they display the property of sustained release of the compound, ara-cytidine, when administered intramuscularly or subcutaneously. Ara-cytidine is known for its anti-viral action and for its usefulness as an agent for controlling leukemias, including acute leukemia, and the sustained release property extends the usefulness of ara-cytidine for these purposes and as an immunosuppressive agent. The 5'-O-derivartives of this invention can also be administered orally.

5 Claims, No Drawings

CYTIDINE NUCLEOSIDE COMPOUND

CROSS REFERENCE TO RELATED APPLICATIONS

This is a division of application Ser. No. 593,890, filed July 7, 1975, now abandoned which is a continuation-in-part of application Ser. No. 427,183, filed Dec. 21, 1973, now abandoned which application is a continuation of application Ser. No. 11,826, filed Feb. 16, 1970, now U.S. Pat. No. 3,847,898, which application is a continuation-in-part of application Ser. No. 828,380, filed May 27, 1969, now abandoned.

In application Ser. No. 745,096, now U.S. Pat. No. 3,547,905 issued Dec. 15, 1970, there is disclosed 1-β-D-arabinofuranosylcytosine 5'-(1-adamantanecarboxylate), described as possessing sustained release properties and a "depot" effect. The compound was synthesized by direct adamantoylation of ara-cytidine to form first the bisadamantoyl compound, and then selective hydrolysis gave the 5'-O-adamantoyl ester.

BACKGROUND OF THE INVENTION

Ara-cytidine, also called cytarabine, cytosine arabinoside, or CA, has been known for some time as an effective agent for controlling growth of certain kinds of cancers, especially leukemia. Its use has been hampered, however, because of difficulties in establishing and maintaining effective and sustained contact between the compound and the cells under treatment.

BRIEF DESCRIPTION OF THE INVENTION

The 5'-O-derivatives, including principally esters, of this invention are prepared by first blocking or protecting the primary amino nitrogen or ara-cytidine with β,β,β-trihaloethoxycarbonyl group wherein "halo" is chlorine or bromine, and "halide" is chloride, bromide or iodide, and then causing the blocked compound to react with an agency capable of reacting with the 5'-O-hydroxyl substituent. There result the 5'-O-derivatives of this invention. The method of this invention, which provides an effective blocking of the primary amino nitrogen, is less wasteful of esterifying agent, and being higher overall-yielding, is also less wasteful of the expensive substance, ara-cytidine. The method renders available a wide range of novel and useful 5'-O-derivatives as will be discussed below.

The compounds of this invention include salts of the 5'-O-derivatives with pharmaceutically acceptable mineral or organic acids having a pK about or less than 2.

The compounds of this invention when administered exhibit the properties characteristic of ara-cytidine, and in addition exhibit the desirable property of sustained release of ara-cytidine over periods of time after administration. Thus the modes of administration and dosages for use are those conventionally used with ara-cytidine. For example, they can be administered orally or intramuscularly. Their use intravenously is feasible, but the need for such disadvantageous devices as the intravenous drip is obviated by the sustained release of "depot" effect of the novel compounds.

In addition, the compounds of this invention exhibit antiphage properties, and, used in conjunction with a deaminase inhibitor, can be used to protect a fermentation threatened with contamination by a phage.

The ester compounds of this invention have the activities and uses that characterize the unesterified compound, cytarabine or ara-cytidine, namely, activity against acute leukemia and against lymphosarcoma, as disclosed in U.S. application Ser. No. 627,645, filed Apr. 3, 1967, now U.S. Pat. No. 3,444,294. As in the case of ara-cytidine sterile injectable solutions such as in cottonseed oil. peanut oil, and sesame seed oil, or dispersions or sterile non-aqueous solutions or dispersions in water, aqueous saline solutions or dispersions suited for injectable use, or sterile powders suited for extemporaneous preparation of sterile injectable solutions or dispersions can be prepared, using the ester compound of this invention. Such solutions are prepared by incorporating the ester compound in the solvent or dispersion medium together with appropriate particle coating agents, surfactants, antibacterial or antifungal agents, isotonic agents and the like. Powders can be prepared by freeze-drying such an appropriately prepared solution or dispersion. Dosage unit forms such as vials and ampules are feasible. The dosage depends on age, weight, and severity of condition of the subject, route and frequency of administration, and can vary from 0.1 to about 50 mgs./kg., or a daily total dose of about 3 to about 4000 mgs., given singly or in divided doses. A unit dosage can contain the ester compound of this invention from about 3 to about 1000 mgs. per unit. This can be from about 0.5% to 25% w/v of the total composition. Utilizing the sustained release characteristic of the ester compounds of this invention, unit doses can be prepared and administered intramuscularly in amounts varying from about 0.5 to about 10 grams or more total dosage, or from about 10 to about 50 mgs./kg. of more. The amount of ester compound in such dosage can vary up to that indicated as sufficient to aid regression and palliation of the leukemia. Thus a 50 mg./kg. dosage can be given once weekly or doses which can be larger can be administered at wider spaced time intervals.

For oral administration, either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the active compound of the formulation with an inert pharmaceutical diluent and filling the mixture into a hard gelatin capsule of appropriate size. In another embodiment, capsules are prepared by filling hard gelatin capsules with polymer coated beads containing the active compound. Soft gelatin capsules are prepared by machine encapsulation of a slurry of the active compound with an acceptable vegetable oil, light liquid petrolatum or other inert oil.

Fluid unit dosage forms for oral administration such as syrups, elixirs, and suspensions can also be prepared. The water-soluble forms of the active compound can be dissolved in an aqueous vehicle together with sugar, aromatic flavoring agents and preservatives to form a syrup. An elixir is prepared by using a hydro-alcoholic (ethanol) vehicle with suitable sweeteners such as sucrose together with an aromatic flavoring agent. Suspensions can be prepared of the insoluble forms with a syrup vehicle with the aid of a suspending agent such as acacia, tragacanth, methylcellulose and the like.

The process of this invention is generally one of esterification and may be shown illustratively in the following reactions wherein X is chloro or bromo:

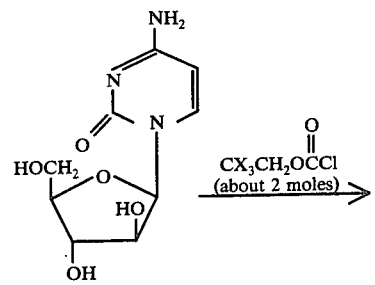

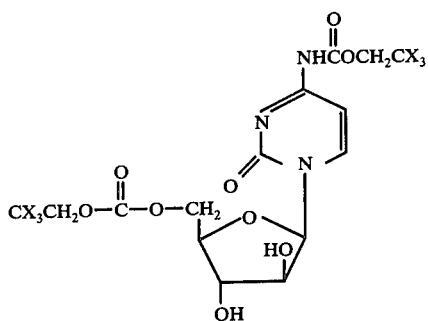

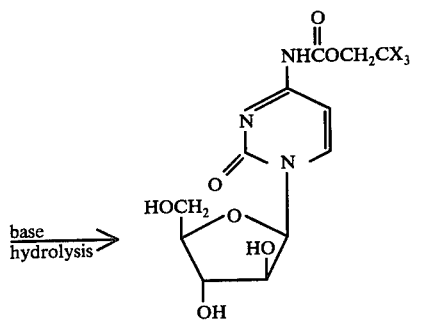

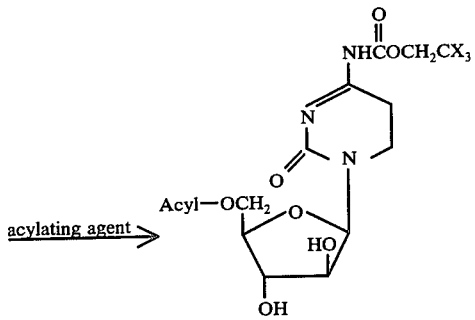

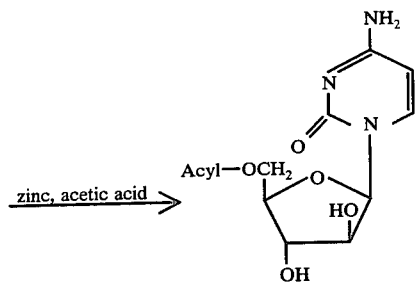

In the above reaction, variations can be made in a number of the stages. For example, the intermediate compound:

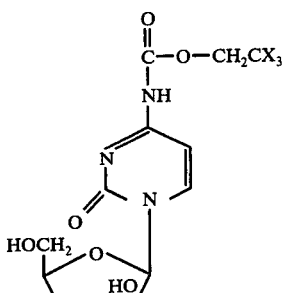

can be made by reaction of 5'-O-trityl-ara-cytidine with β,β,β-trihaloethoxycarbonyl halide to form the analogous N-derivative, and subsequently removing the trityl group by known methods.

The reaction is given illustratively as follows:

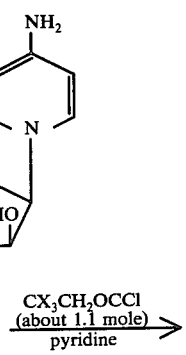

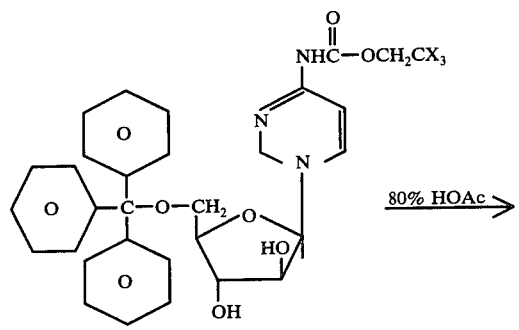

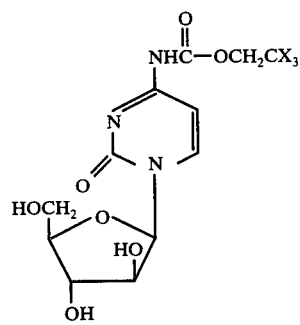

5'-O-Trityl ara-cytidine can be used as starting material for the following alternative reactions in which an excess of β,β,β-trichloroethoxycarbonyl chloride is used:

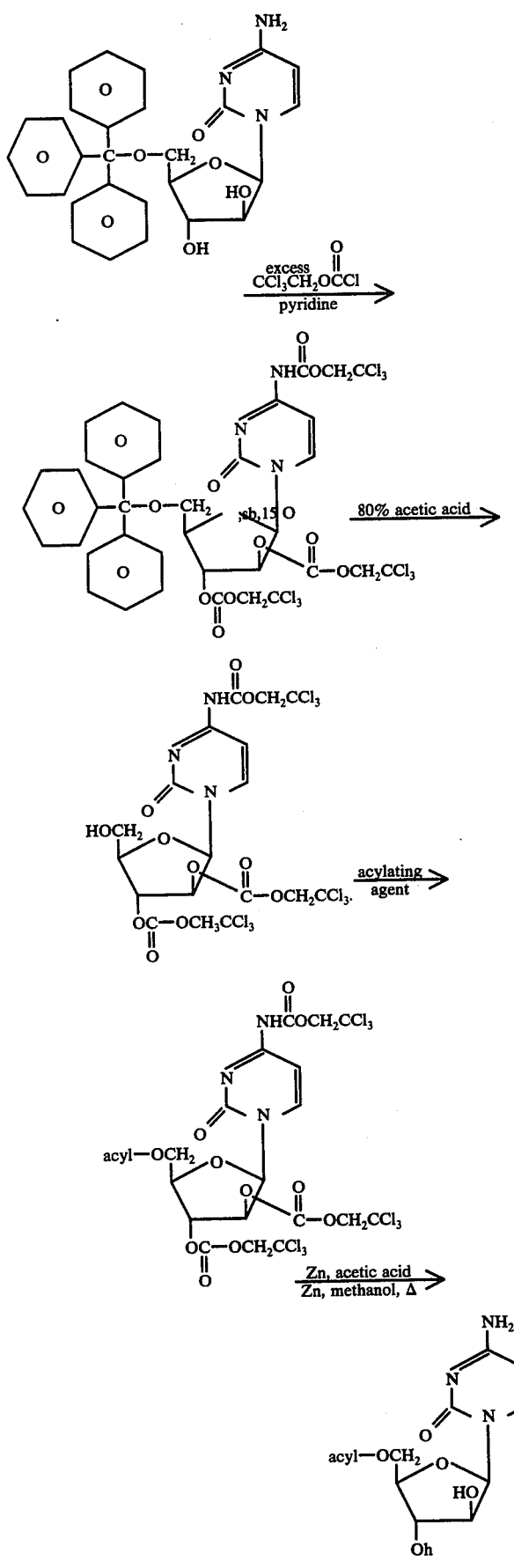

In practicing the invention, and as is disclosed in more detail in the foregoing and ensuing description, the process involves use of a novel class of intermediates having the following structural formula:

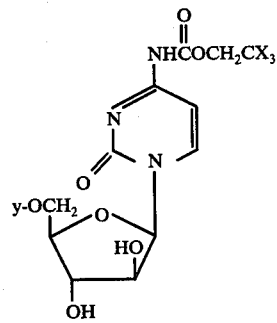

in wich y=H, trityl or an acyl radical. These intermediates, where y=H are capable of being transformed into the wide class of esters disclosed in this application, protected as shown at the amino nitrogen. The esters, too, are intermediates and constitute the compounds of the above formula where y=acyl. These ester intermediates are further capable of being transformed by removal of the protective group on the amino nitrogen into the free amino ester product compounds possessing the aforesaid valuable pharmacological properties, as will be seen from the following description and examples.

Alternatively, the primary amino group of ara-cytidine may be protected from concomitant acylation by protonation. This is done by reacting ara-cytidine with the acylating agent, for example, an acyl halide or acyl anhydride in the presence of a sufficiently high hydrogen ion concentration, so that the primary amino group of ara-cytidine is protected. It has been found in this invention that the amino group in such amino protected nucleoside species is resistant to conventional acylation procedures.

In the above equations, of particular value and interest in the general sense are those in which the substituent acyl is that of an organic carboxylic acid,

in which R can have a wide range of values. For example, R can broadly mean a straight- or branched-chain aliphatic radical containing from 1 to 20 carbon atoms which can be substituted by halogen, hydroxyl, carboxyl or mercapto groups, a monocyclic or bicyclic aromatic radical of from 6 to 10 carbon atoms, on a cage-type hydrocarbon radical containing from 7 to 20 carbon atoms. R can also denote the variety of substituents that are shown in Table I to XI which follow.

Representative values of R in the foregoing are: methyl, ethyl, t-butyl, 2,2-dimethylpropyl, 1-chloro-2,3-dimethylbutyl, 2,2-dimethylpropyl, 1-mercapto-2,2-dimethylpropyl, phenyl, 2-methylphenyl, 2,6-dimethylphenyl, 2,4,6-trimethylphenyl, 1-naphthyl, 2-naphthyl,

-continued

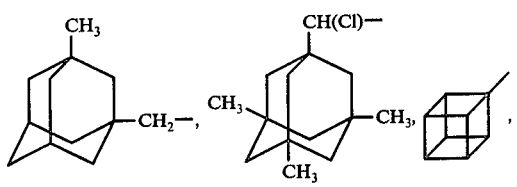

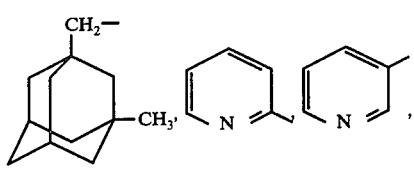

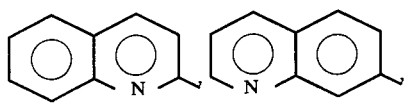

and also groups, which, together with the

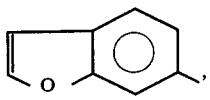

group make up the acyl group of acids such as glutamic, glutaric, succinic, fumaric, aconitic, itaconic, levulinic, 3,3-dimethylglutaric and other 3,3-dialkylglutaric acids and other acids as will be exemplified later.

Of these, of particular application are the classes of N-protected intermediates wherein

in which $R'_1$ is an aliphatic radical of from 1 to 20 carbon atoms, an aromatic radical of from 6 to 10 carbon atoms, a cage-type hydrocarbon radical of from 7 to 20 carbon atoms, a monocyclic aliphatic radical of from 4 to 10 carbon atoms, an araliphatic radical of from 7 to 12 carbon atoms or a monocyclic heterocyclic radical of from 4 to 10 carbon atoms or wherein

is the acyl radical of an aliphatic dicarboxylic acid of from 3 to 8 carbon atoms. Eliminative removal of the amino-protecting group results in the free amino ester product compound corresponding otherwise to the formula immediately above but wherein

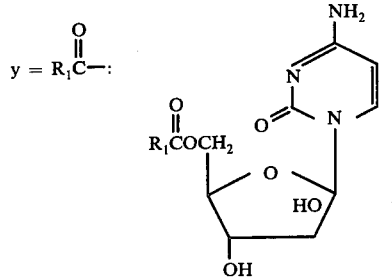

wherein $R_1$ is a radical selected from the group consisting of an aliphatic of from 1 to 20 carbon atoms, aromatic of from 6 to 10 carbon atoms, a monocyclic aliphatic of from 4 to 10 carbon atoms, and araliphatic of from 7 to 12 carbon atoms or a monocyclic heterocyclic of from 4 to 10 carbon atoms; or wherein

is the acyl radical of an aliphatic dicarboxylic acid of 3 to 8 carbon atoms.

One important class of such novel compounds is that wherein the acylating agent used is an acyl halide or an anhydride of an aliphatic acid containing 1 to 18 carbon atoms, such as acetyl chloride or anhydride, isobutyrylbromide or anhydride, caproyl chloride or anhydride, palmityl chloride or anhydride, stearyl chloride or anhydride, lauroyl chloride or anhydride, oleyl chloride or anhydride, myristic chloride or anhydride, isomers thereof and the like.

Another important class of novel compounds of this invention is that wherein the acyl radical of

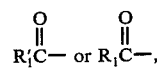

is that of a dicarboxylic aliphatic acid of from 3 to 8 carbon atoms, such as glutaric, 3,3-dialkylglutaric, succinic, itaconic, or fumaric acid, and the like.

In addition to the above, R can also be a substituted amino group in which the substituents can be aliphatic, aromatic, heterocyclic or cage-type radical, as illustrated later. R can also be a mercapto group or an alkylmercapto group, MS- in which M is as illustrated later. The acyl substituent at 5'-O can also be those to form a carbonate ester as illustrated later.

In addition to carboxyl acyl groups the derivative groups attached to the 5'-O oxygen of ara-cytidine can be thio-acyl group such as

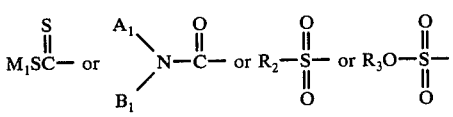

in which $M_1$, $A_1$ and $B_1$, $R_2$ and $R_3$ are as will be illustrated later.

The acyl group attached to the 5'-oxygen of ara-cytidine can also be that of an esterified phosphoric acid such as

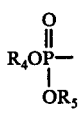

in which the value of $R_4$ and $R_5$ can be an aliphatic or substituted aliphatic as will be illustrated later;

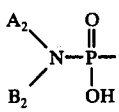

in which the value of $A_2$ and $B_2$ can be hydrogen or aliphatic as will be illustrated later, or

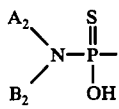

in which the value of $A_2$ and $B_2$ is as given above.

The processes of this invention as described above render possible the preparation of a wide variety of 5'-O-esters of ara-cytidine. Among these products are a number of classes of novel compounds, heretofore unknown, in their free base or salt form which possess as a common property, the advantage of sustained release previously described.

DETAILED DESCRIPTION OF THE INVENTION

In the following tables there are set forth the acylating agents together with the substituent groups of the acylating agents referred to above and the identification of the product ester of ara-cytidine. These agents are reacted with ara-cytidine protected as described above, and in each case the intermediate product containing the $N^4$-trihaloethoxycarbonyl protective group is formed, which group is subsequently removed as described above and in the examples with follow.

A number of acylating agents containing the trichloroethoxycarbonyl group as a substituent are given illustratively in the tables. It is to be understood that such substituted acylating agents can be prepared by reaction with trichloroethoxycarbonyl chloride as described above (for ara-cytidine and related compounds) and as illustrated in the following examples. The trichloroethoxycarbonyl groups of such 5'-O-acyl radicals are removed along with the trihaloethoxycarbonyl group protecting the amino group of ara-cytidine in the final eliminative step of the process.

The acid chlorides of the carboxylic acids, used as acylating agents, can be prepared by conventional methods, as for example, by reaction of the acid RCOOH (a) with $SOCl_2$ (b) with $PCl_5$, or (c) with $POCl_3$. The method (a) is suitable for most acids except those which boil within 5°–10° C. of $SOCl_2$, in which case, the method (c) is suitable.

It is further to be understood that the acid RCOOH can be transformed to an active acylating agency by first reacting it with p-toluenesulfonyl chloride, and this reaction product (tosylate) can be used in place of the anhydride or chloride, in accordance with the procedures described in J. Am. Chem. Soc. 77, 6214 (1955).

Analogous to the above acid RCOOH can be transformed to an acylating agency by first reacting it with $(CF_3CO)_2O$, and then using the product as acylating agent, in accordance with the procedures described in Chem. Rev. 55, 787 (1955).

A further esterification procedure which is suitable is to use the acid RCOOH directly, carrying out the reaction in the presence of dicyclohexylcarbodiimide, in accordance with the procedures described in Compt. Rend. 252, 896 (1961); Ibid. 255, 945 (1962); J. Org. Chem. 27, 4075 (1962) and Tetrahedron 21, 3531 (1965).

For acylation of ara-cytidine only at the 5'-O position, according to this invention, coincident acylation of the amino group at position 4 must be prevented. This is done by first protecting the amino group by a suitable protective agent. In one form of the invention process, this is accomplished by reacting ara-cytidine with a trihaloethoxycarbonyl halide, in which "halo" is chlorine or bromine, and "halide" is chloride, bromide or iodide. Exemplary reagents are trichloroethoxycarbonyl chloride (Aldrich Chemical Co., Milwaukee, Wisconsin) and tribromoethoxycarbonyl chloride [J. Org. Chem. 33, 3589-93 (1968)].

When ara-cytidine is reacted with the appropriate molar proportion (about 2) of trihaloethoxycarbonyl halide, the intermediate product $N^4,5'$-O-bis-trihaloethoxycarbonyl ara-cytidine is formed. This reaction is previously shown. The reaction can be carried out in pyridine, and the product recovered by removal of the solvent by distillation. The reaction conditions for protective group removal described in Example 1 can be followed.

The $N^4$, 5'-O-bis-trihaloethoxycarbonyl ara-cytidine can be hydrolyzed by treatment with dilute sodium hydroxide. The compound dissolved in tetrahydrofuran is treated with an equal volume of sodium hydroxide solution, about 0.3 N, let stand at room temperature to equilibrate, and then is neutralized with acetic acid. The product, $N^4$-trihaloethoxycarbonyl ara-cytidine, can be removed by crystallization and purified by recrystallization from acetone.

Advantageously, $N^4$-trihaloethoxycarbonyl ara-cytidine can be prepared by reacting 5'-O-trityl ara-cytidine (U.S. Pat. No. 3,338,832, Example 1) with $N^4$-trihaloethoxycarbonyl halide (THEC halide) (Example 1). The reaction is conducted in dry pyridine at low temperature, about −5° to 5°, preferably about 3° C. If the molar proportion of 5'-O-trityl ara-cytidine to THEC halide is about 1:1, the reaction product is $N^4$-trihaloethoxycarbonyl-5'-O-trityl-ara-cytidane. If an excess of THEC halide is used, i.e., a molar proportion less than 1:3, preferably about 1:4 to 1:5, the reaction product is $N^4$-2',3'-O-tris-trihaloethoxycarbonyl-5'-O-trityl-ara-cytidine. The solvent is removed and the residue is extracted into a chlorinated hydrocarbon solvent, e.g., methylene chloride, and washed with water. In the case where the reaction product is tris-trihaloethoxycarbonyl-5'-O-trityl-ara-cytidine, the protective group at 2'-O and 3'-O can be removed at this point, if desired, by hydrolysis with a base, e.g., 0.15 N sodium hydroxide in 50% tetrahydrofuran-50% water, to give the $N^4$-monoprotected 5'-O-trityl product which is isolated. Alternatively, the washed residue in a chlorinated hydrocarbon solvent is evaporated. If desired, the THEC-protected, tritylated products can be recrystallized from suitable solvents, e.g., methylene chloride or acetone. The protected intermediates, mono- or tris-THEC 5'-O-trityl CA derivatives, are treated with 80% acetic acid as illustrated in Example 2 to remove the 5'-O-trityl group to yield the intermediate, $N^4$-trihaloethoxycarbonyl ara-cytidine.

By acylation at the 5'-O position by use of the acylating agents exemplified by Tables I to XI and illustrated in the examples, there are produced the novel amino protected 5'-O-esters of ara-cytidine of the invention. The protective group is removable by treatment with metallic zinc in methanol solution of the ester; by treatment with metallic zinc, for example as zinc dust, and acetic acid, for example, in 80 to 90% acetic acid solution; or by treatment with zinc chloride or zinc acetate in methanol.

The water solubility of the 5'-O-derivatives of this invention can be improved and thus their pharmaceutical versatility is enhanced by conversion to their salt form with pharmaceutically accepted acids which have a pK about or less than 2. These acids can be broadly classed as the strong mineral or organic acids, and this class of acids are appropriate because ara-cytidine and the 5'-O-derivatives of it which characterizes this invention are weak bases. Examples of the strong acids are hydrochloric, sulfuric, phosphoric, glutaric, glutamic, tartaric, trihydroxybenzoic, formic and the like. They are formed by suspending the desired 5'-O-derivatives in a medium such as methanol and adding appropriately one equivalent of the desired acid. The result is a solution of the acid salt, which can be caused to separate by the adding of appropriate media such as diethyl ether. The salts can be purified by recrystallization from solvent mixtures such as methanol:ether. The hydrohalide salt can also be obtained by simply not neutralizing the acylation mixture resulting from the reaction of RCOCl before isolating the acylated product from the solvent.

In Table I, below, are given, illustratively, typical acylating agents and resulting ara-cytidine-5'-O-acylate products for the case when the acyl group is $$R'\overset{O}{\underset{\|}{C}}-,$$

wherein $R_1$ is as defined previously.

TABLE I

R of RCO = $R_1$

| No. | $R_1$ | Acylating Agent | Product |
|---|---|---|---|
| 1 | $CH_3-$ | Acetic anhydride or acetyl chloride | 5'-O-acetyl ara-cytidine |
| 2 | $(CH_3)_3C-$ | Pivaloyl chloride | 5'-O-pivaloyl ara-cytidine |
| 3 | $(CH_3)_2CH-$ | Isobutyryl chloride | 5'-O-isobutyryl ara-cytidine |
| 4 | $CH_3(CH_2)_7-$ | Octanoyl chloride (caproyl chloride) | 5'-O-octanoyl ara-cytidine |
| 5 | $CH_3(CH_2)_{14}-$ | Palmityl chloride | 5'-O-palmityl ara-cytidine |
| 6 | $CH_3(CH_2)_{16}-$ | Stearyl chloride | 5'-O-stearyl ara-cytidine |
| 7 | $CH_3(CH_2)_7CH=CH(CH_2)_7-$ | Oleyl chloride | 5'-O-oleyl ara-cytidine |
| 8 | $ClCH_2\underset{CH_3}{\overset{CH_3}{\underset{\|}{\overset{\|}{C}}}}-$ | β-chloropivaloyl chloride | 5'-O-(β-chloropivaloyl) ara-cytidine |
| 9 | p-nitrophenyl (NO$_2$-C$_6$H$_4$-)  | p-nitrobenzoyl chloride | 5'-O-p-nitrobenzoyl ara-cytidine |
| 10 | o-tolyl (CH$_3$-C$_6$H$_4$-) | o-toluoyl chloride | 5'-O-toluoyl ara-cytidine |
| 11 | phenyl (C$_6$H$_5$-) | Benzoyl chloride | 5'-O-benzoyl ara-cytidine |
| 12 | 2,6-dimethylphenyl | 2,6-dimethylbenzoyl chloride | 5'-O-(2,6-dimethylbenzoyl) ara-cytidine |
| 13 | 2,4,6-trimethylphenyl | 2,4,6-trimethylbenzoyl chloride | 5'-O-(2,4,6-trimethylbenzoyl) ara-cytidine |

TABLE I-continued

| No. | $R_1$ | Acylating Agent | Product |
|---|---|---|---|
| 14 | (1-fluorenyl group) | 1-fluorene carbonyl chloride | 5'-O-(1-fluorene carbonyl) ara-cytidine |
| 15 | (9-fluorenyl group) | 9-fluorene carbonyl chloride | 5'-O-(9-fluorene carbonyl) ara-cytidine |
| 16 | (1-naphthyl group) | 1-naphthoyl chloride | 5'-O-(1-naphthoyl) ara-cytidine |
| 17 | (1-indenyl group) | 1-indene-carbonyl chloride | 5'-O-1-indene-carbonyl ara-cytidine |
| 18 | $CH_3O$—(phenyl)— | p-anisoyl chloride | 5'-O-p-anisoyl ara-cytidine |
| 19 | 3,4,5-trimethoxyphenyl ($OCH_3$, $CH_3O$, $OCH_3$) | 3,4,5-trimethoxybenzoyl chloride | 5'-O-(3,4,5-trimethoxybenzoyl) ara-cytidine |
| 20 | $CH_3$—(phenyl)— | p-toluoyl chloride | 5'-O-p-toluoyl ara-cytidine |
| 21 | (1-norbornyl group) | 1-norbornanecarbonyl chloride | 1-norbornylcarbonyl ara-cytidine |
| 22 | (2-norbornyl group) | exo- or exo/endo-mixture of 2-norbornanecarbonyl chloride | exo- or exo/endo-mixture of 5'-O-(2-norbornylcarbonyl)ara-cytidine |
| 23 | (7-norbornyl group) | 7-norbornane carbonyl chloride | 5'-O-(7-norbornyecarbonyl) ara-cytidine |
| 24 | (2-adamantyl group) | 2-adamantane carbonyl chloride | 5'-O-2-adamantyl-carbonyl ara-cytidine |
| 25 | (1-adamantyl)-$CH_2$— | 1-adamantyl acetyl chloride | 5'-O-(1-adamantyl acetyl) ara-cytidine |
| 26 | 3,5,7-trimethyl-1-adamantyl-CHCl— ($CH_3$, $CH_3$, $CH_3$, Cl) | [α-chloro-3,5,7-trimethyl-1-adamantyl acetyl]chloride | 5'-O-[(α-chloro-3,5,7-trimethyl-1-adamantyl)acetyl] ara-cytidine |

TABLE I-continued

| No. | R₁ | Acylating Agent | Product |
|---|---|---|---|
| 27 | (cubane) | pentacyclo[4.2.0.0$^{2,5}$.0$^{3,8}$.0$^{4,7}$]octane carbonyl chloride (cubane carbonyl chloride) | 5'-O-pentacyclo-[4.3.0.0$^{2,5}$.0$^{3,8}$.0$^{4,7}$]octyl-carbonyl ara-cytidine |
| 28 | (cyclobutane) | cyclobutane carboxylic acid anhydride | 5'-O-cyclobutyl-carbonyl ara-cytidine |
| 29 | (cyclopentane) | cyclopentane carbonyl chloride | 5'-O-cyclopentyl-carbonyl ara-cytidine |
| 30 | (cyclohexane) | cyclohexane carbonyl chloride | 5'-O-cyclohexyl-carbonyl ara-cytidine |
| 31 | (pyridine) | picolinyl chloride | 5'-O-picolinyl ara-cytidine |
| 32 | (tetrahydrofuran) | tetrahydrofuroyl chloride (tetrahydropyromuconyl chloride) | 5'-O-tetrahydro-2-furoyl ara-cytidine |
| 33 | (xanthene) | 9-xanthene carbonyl chloride | 5'-O-(9-xanthenyl-carbonyl) ara-cytidine |
| 34 | (pyridine) | nicotinyl chloride | 5'-O-nicotinoyl ara-cytidine |
| 35 | (6-methoxyquinoline) | 6-methoxy-4-quinoline carbonyl chloride (quininyl chloride) | 5'-O-(6-methoxy-4-quinolylcarbonyl) ara-cytidine |
| 36 | (cinnoline) | 4-cinnoline carbonyl chloride | 5'-O-(4-cinnolyl-carbonyl) ara-cytidine |
| 37 | (thiophene) | 2-thiophene carbonyl chloride | 5'-O-(2-thenoyl) ara-cytidine |
| 38 | (thianaphthene-CH₂-) | 4-thianaphthene acetyl chloride | 5'-O-(4-thianaphthene acetyl) ara-cytidine |
| 39 | (furan) | 2-furoyl chloride | 5'-O-2-furoyl ara-cytidine |
| 40 | (5-bromofuran) | 5-bromo-2-furoyl chloride | 5'-O-(5-bromo-2-furoyl) ara-furoyl)ara-cytidine |
| 41 | (coumalyl) | coumalyl chloride | 5'-O-coumalyl ara cytidine |
| 42 | (coumarin-3-yl) | coumarin-3-carbonyl chloride | 5'-O-coumarin-3-carbonyl ara-cytidine |

TABLE I-continued

| No. | R₁ | Acylating Agent | Product |
|---|---|---|---|
| 43 | 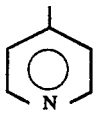 | isonicotinoyl chloride | 5'-O-isonicotinoyl ara-cytidine |
| 44 |  | 2-quinuclidine carbonyl chloride | 5'-O-(2-quinuclidinylcarbonyl) ara-cytidine |
| 45 |  | 3-quinuclidine carbonyl chloride | 5'-O-(3-quinuclidinylcarbonyl) ara-cytidine |
| 46 |  | 4-quinuclidine carbonyl chloride | 5'-O-(4-quinuclidinylcarbonyl) ara-cytidine |
| 47 |  | N-trichloroethoxycarbonyl-2-pyrrole carbonyl chloride | 5'-O-(2-pyrrolylcarbonyl) ara-cytidine |
| 48 | 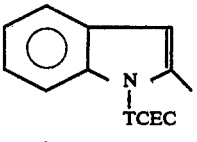 | N-trichloroethoxycarbonyl-2-indole carbonyl chloride | 5'-O-(2-indolylcarbonyl) ara-cytidine |
| 49 | 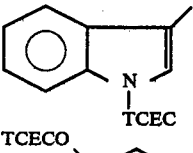 | N-trichloroethoxycarbonyl-3-indole carbonyl chloride | 5'-O-(3-indolylcarbonyl) ara-cytidine |
| 50 | TCECO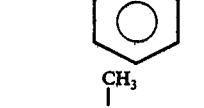 | hydroxybenzoyl chloride trichlorocarbonate | 5'-O-hydroxybenzoyl ara-cytidine |
| 51 | 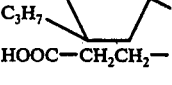 | trans-3-(n-propyl)-hygric acid chloride, hydrochloride | 5'-O-trans-[3-(n-propyl)hygroyl]-ara-cytidine |
| 52 | HOOC—CH₂CH₂— | succinic anhydride | 5'-O-hemisuccinyl ara-cytidine |
| 53 | 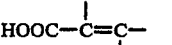 | fumaryl chloride | 5'-O-hemifumaryl ara-cytidine |
| 54 | 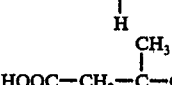 | 3,3-dimethylglutaric anhydride | 5'-O-hemi(3,3-dimethylglutaryl) ara-cytidine |
| 55 | 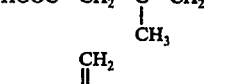 | itaconic anhydride | 5'-O-itaconyl ara-cytidine |
| 56 | 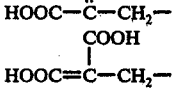 | aconitic anhydride | 5'-O-aconityl ara-cytidine |

*TCEC means the trichloroethoxycarbonyl radical.

In Table II, below, are given typical acylating agents and resulting products in the case when the acyl group is

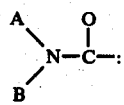

TABLE II

(R of RCO= A\N—/B)

| A | B | Acylating Agent | Final Product |
|---|---|---|---|
| H— | H— | N-carbonylsulfamic acid chloride, sodium cyanide and trifluoro-acetic acid | 5'-O-(carbamoyl)-ara-cytidine |
| H— | $CH_3CH_2$— | ethyl isocyanate | 5'-O-(ethylcarbamoyl)-ara-cytidine |
| H— | cyclohexyl | cyclohexyl isocyanate | 5'-O-(cyclohexylcarbamoyl)-ara-cytidine |
| H— | $CH_3(CH_2)_7$— | n-octyl isocyanate | 5'-O-(n-octylcarbamoyl)-ara-cytidine |
| $C_2H_5$— | $C_2H_5$— | diethylamine and phosgene | 5'-O-(diethylcarbamoyl)ara-cytidine |
| n-$C_4H_9$— | n-$C_4H_9$— | di-n-butylamine and phosgene | 5'-O-(di-n-butylcarbamoyl)-ara-cytidine |
| $CH_2$=CH—$CH_2$— | phenyl | N-allylaniline and phosgene | 5'-O-(N-allyl-N-phenylcarbamoyl)-ara-cytidine |
| (pentamethylene) | | pipyridine + phosgene | 5'-O-(N,N-pentamethylenecarbamoyl)-ara-cytidine |

In the foregoing formula, A and B are the same or different radicals selected from the group consisting of H, aliphatic of from 1 to 10 carbon atoms, monocyclic aliphatic of from 4 to 10 carbon atoms, and aromatic of from 6 to 10 carbon atoms, or in which A and B together make up an aliphatic chain of from 3 to 6 carbon atoms.

In the case where R of RCO = MS, general procedures for preparing the substituted monothiol chlorocarbonates as acylating agents are given in J. Am. Chem. Soc. 82, 4347 (1960) and Monatsch. Chem. 81, 939 (1950). Briefly the mercaptan MSH is reacted with $COCl_2$ in the presence of $NiCl_3$ to produce the acylating agent $$\overset{O}{\underset{\|}{MSCCl}}$$

In this class M is a radical selected from the group consisting of aliphatic of from 1 to 10 carbon atpms, monocyclic aliphatic of from 4 to 10 carbon atoms, and aromatic of from 6 to 10 carbon atoms, and aralkyl from 7 to 12 carbon atoms. Representative acylating agents of this kind and the resulting final products are:

TABLE III

| M | Mercaptan Reagent (+$COCl_2$) | Final Product |
|---|---|---|
| benzyl ($C_6H_5$-$CH_2$—) | benzyl mercaptan | ara-cytidine 5'-S-benzylthiocarbonate |
| $(CH_3)_2CH$— | isopropyl mercaptan | ara-cytidine 5'-S-isopropylthiocarbonate |
| $CH_3(CH_2)_3$— | n-butyl mercaptan | ara-cytidine 5'-S-n-butylthiocarbonate |
| $CH_2$=$CHCH_2$— | allyl mercaptan | ara-cytidine 5'-S-allylthiocarbonate |
| phenyl | benzenethiol | ara-cytidine 5'-S-phenylthiocarbonate |
| pentachlorophenyl | pentachlorothiophenol | ara-cytidine 5'-S-pentachlorophenylthiocarbonate |
| cyclohexyl | cyclohexylmercaptan | ara-cytidine 5'-S-cyclohexylthiocarbonate |
| $CH_3(CH_2)_9$— | n-decyl mercaptan | 5'-ara-cytidine 5'-S-n-decylthiocarbonate |

Where the acyl radical attached to the 5' oxygen of ara-cytidine is $$\overset{S}{\underset{\|}{M_1SC—,}}$$

the acylating agent can be prepared in a manner analogous to the above, substituting thiophosgene ($CSCl_2$) for $CDCl_2$. In this class $M_1$ is a radical selected from the group consisting of aliphatic of from 1 to 10 carbon atoms, aromatic of from 6 to 10 carbon atoms, and aralphatic of from 7 to 12 carbon atoms. Representative acylating agents of this kind and the resulting final products are:

TABLE IV

| $M_1$ | Mercaptan Reagent (+ $CSCl_2$) | Final Product |
|---|---|---|
| $C_2H_5$— | ethyl mercaptan + thiophosgene | ara-cytidine 5'-S-ethyl xanthate |

TABLE IV-continued

| $M_1$ | Mercaptan Reagent (+ $CSCl_1$) | Final Product |
|---|---|---|
| | phenyl thiol + thiophosgene | ara-cytidine 5'-S-phenyl xanthate |
| 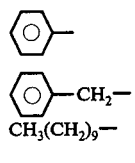 | benzyl thiol + thiophosgene | ara-cytidine 5'-benzyl xanthate |
| $CH_3(CH_2)_9$— | decyl thiol + thiophosgene | 5'-ara-cytidine 5'-S-decyl xanthate |

Where the acyl radical attached to the 5'-oxygen of ara-cytidine is

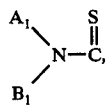

the preparation is by the reaction of the class of products of Table IV, (i.e., where the acyl radical attached to the 5'-oxygen of ara-cytidine is $$\overset{S}{\underset{\|}{M_1SC-}}),$$

with $A_1B_1NH$. General procedures for carrying out this reaction are given in J. Chem. Soc., 2195 (1951). In this class $A_1$ and $B_1$ are the same or different radicals selected from the group consisting of H, alkyl of from 1 to 7 carbon atoms, and aromatic of from 6 to 10 carbon atoms.

Representative compounds involved in this method are:

TABLE V

| $R_1$ | $R_2$ | Reagent | Final Product |
|---|---|---|---|
| H— | H— | ammonia | 5'-O-(thiocarbamoyl)ara-cytidine |
| $CH_3$— | H— | methyl amine | 5'-O-(methyl thiocarbamoyl)ara-cytidine |
| $C_2H_5$— | H— | ethyl amine | 5'-O-(ethyl thiocarbamoyl)ara-cytidine |
| $CH_3$— | $CH_3$— | dimethyl amine | 5'-O-(dimethyl thiocarbamoyl)ara-cytidine |
| $C_2H_5$— | $C_2H_5$— | diethyl amine | 5'-O-(diethyl thiocarbamoyl)ara-cytidine |
|  | $CH_3$— | N-methyl aniline | 5'-O-(methylphenylthiocarbamoyl)-ara-cytidine |

Where the acyl radical attached to the 5'-oxygen of ara-cytidine is $$\overset{O}{\underset{\underset{O}{\|}}{\overset{\|}{R_2-S-}}},$$

the preparation is analogous to that of using the carboxylic acid chlorides, but using the appropriate sulfonyl chloride. In this class $R_2$ is a radical selected from the group consisting of alkyl of from 1 to 7 carbon atoms, aromatic of from 6 to 10 carbon atoms, and substituted aromatic of from 6 to 12 carbon atoms. Representative acylating agents and final products are:

TABLE VI $$(R_2\overset{\overset{O}{\|}}{\underset{\underset{O}{\|}}{-S-}})$$

| $R_2$ | Acylating Agent | Final Product |
|---|---|---|
| $CH_3$— | methanesulfonylchloride | 5'-O-methylsulfonyl-ara-cytidine |
|  | benzenesulfonyl chloride | 5'-O-phenylsulfonyl-ara-cytidine |
| Br—⌬— | p-bromobenzenesulfonyl chloride | 5'-O-(p-bromophenylsulfonyl)ara-cytidine |
| $NO_2$—⌬— | p-nitrobenzenesulfonyl chloride | 5'-O-(p-nitrophenylsulfonyl)ara-cytidine |
| $CH_3$—⌬— | p-toluenesulfonyl chloride | 5'-O-(p-tolylsulfonyl)-ara-cytidine |
| $(CH_3)_2CH$—⌬—$CH(CH_3)_2$ with $CH(CH_3)_2$ | 2,4,6-triisopropylbenzenesulfonyl chloride | 5'-(2,4,6-triisopropylphenylsulfonyl)ara-cytidine |

Where the acyl radical attached to the 55'-oxygen of ara-cytidine is

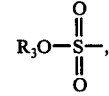

the preparation of the acylating agent is by the known method of reacting ROH with $SOCl_2$ to produce the acylating agent $$R_3O-\overset{\overset{O}{\|}}{\underset{\underset{O}{\|}}{S}}-Cl,$$

which is then used analogously to the carboxylic acid chlorides. In this class $R_3$ is a radical selected from the group consisting of aliphatic of from 1 to 20 carbon atoms, aromatic of from 6 to 10 carbon atoms, and araliphatic of from 7 to 12 carbon atoms. Representative compounds involved are:

TABLE VII $$(R_3O-\overset{\overset{O}{\|}}{\underset{\underset{O}{\|}}{S}}-)$$

| $R_3$ | Reagent (+SOCl$_2$) | Final Product |
|---|---|---|
| H— | sulfur trioxide | ara-cytidine 5'-sulfate |
| CH$_3$— | methanol + thionyl chloride | ara-cytidine 5'-methyl sulfate |
| C$_2$H$_5$— | ethanol + thionyl chloride | ara-cytidine 5'-ethyl sulfate |
| 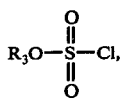 | phenol + thionyl chloride | ara-cytidine 5'-phenyl sulfate |
| 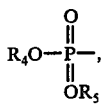—CH$_2$— | benzyl alcohol + thionyl chloride | ara-cytidine 5'-benzyl sulfate |
| n-CH$_3$(CH$_2$)$_{17}$— | n-octadecyl alcohol + thionyl chloride | ara-cytidine 5'-octadecyl sulfate |

Where the acyl radical attached to the 5'-oxygen of ara-cytidine is $$R_4O-\overset{\overset{O}{\|}}{\underset{\underset{OR_5}{|}}{P}}-,$$

the preparation of the acylating agent can be carried out by known methods. General procedures using an aliphatic alcohol in combination with dicyclohexylcarbodiimide and phosphorus oxychloride (POCl$_3$) are described is J. Am. Chem. Soc. 80, 6212 (1958). General procedures using di-substituted ($R_4$ and $R_5$) phosphorchloridates as acylating agents are described in Angew. Chem. Internat. Edit. 6, 362 (1967). General procedures using substituted phosphates ($R_4$) and dicyclohexylcarbodiimide are described in Chem. Ber. 100, 2228 (1967). In this class $R_4$ and $R_5$ are the same or different radicals selected from the group consisting of alkyl of from 1 to 7 carbon atoms and haloalkyl of from 1 to 7 carbon atoms. Representative compounds involved are:

TABLE VIII $$(R_4O-\overset{\overset{O}{\|}}{\underset{\underset{OR_5}{|}}{P}}-)$$

| $R_4$ | $R_5$ | Reactants | Final Products |
|---|---|---|---|
| H— | CCl$_3$CH$_2$— | β,β,β-trichloroethylphosphate + DCC | β,β,β-trichloroethyl-(5'-ara-cytidylate) |
| CH$_3$CH$_2$— | CH$_3$CH$_2$— | diethylphosphoro chloridate | diethyl-(5'-ara-cytidylate) |
| CCl$_3$CH$_2$— | CCl$_3$CH$_2$— | bis-β,β,β-trichloroethyl-phosphoro chloridate | bis-β,β,β-trichloroethyl-5'-ara-cytidylate) |

Where the acyl radical attached to the 5'-oxygen of ara-cytidine is $$R_6O-\overset{\overset{O}{\|}}{C}-,$$

the acylating agent is $$R_6O-\overset{\overset{O}{\|}}{C}-Cl,$$

and the acylation is carried out following known procedures for the preparation of carbonate esters. In this class $R_6$ is a radical selected from the group consisting of aliphatic of from 1 to 20 carbon atoms, aromatic of from 6 to 10 carbon atoms, and araliphatic of from 7 to 12 carbon atoms. Representative compounds are:

TABLE IX $$(R_6O-\overset{\overset{O}{\|}}{C}-)$$

| $R_6$ | Reagent | Product |
|---|---|---|
| CH$_3$— | methyl chloroformate | ara-cytidine 5'-methyl carbonate |
| C$_2$H$_5$— | ethyl chloroformate | ara-cytidine 5'-ethyl carbonate |
| 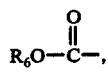—CH$_2$— | carbobenzoxy chloride | ara-cytidine 5'-phenyl carbonate |
| CH$_3$(CH$_2$)$_7$— | octyl chloroformate | octanyl (5'-ara-cytidylyl)carbonate |
| CH$_3$(CH$_2$)$_{15}$— | hexadecyl chloroformate | ara-cytidine 5'-hexadecyl carbonate |
| 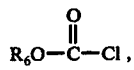 | phenyl chloroformate | ara-cytidine 5'-phenyl carbonate |

Where the acyl radical attached to the 5'-oxygen of ara-cytidine is

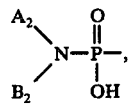

the final product is prepared by reacting the intermediate compound, produced as described above in connection with Table VIII, N$^4$-trichloroethoxycarbonyl-ara-cytidine-5'-phosphate, with the appropriate amine compound in the presence of dicyclohexylcarbodiimide. General analogous procedures are described in J. Am. Chem. Soc. 80, 3752 (1958). In this class $A_2$ and $B_2$ are the same or different radicals selected from the group consisting of H and alkyl of from 1 to 7 carbon atoms. Representative compounds involved are:

shows a single, ultraviolet-absorbing spot on thin layer chromatography and is essentially analytically pure.

TABLE X

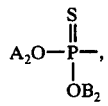

| $A_2$ | $B_2$ | Amine | Final Product |
|---|---|---|---|
| H— | H— | (NTCEC) p$\mathrm{\overset{|}{C}}$a + D$\mathrm{\overset{||}{C}}$C + ammonia | ara-cytidine 5'-phosphoramidate |
| $CH_3$ | H— | \| + \|\| + methyl amine | ara-cytidine 5'-(methyl phosphoramidate) |
| $C_2H_5$— | H— | \| + \|\| + ethyl amine | ara-cytidine 5'-(ethyl phosphoramidate) |
| $CH_3$— | $CH_3$— | \| + \|\| + dimethyl amine | ara-cytidine 5'-(dimethyl phosphoramidate) |
| $C_2H_5$— | $C_2H_5$— | \| + \|\| + diethyl amine | ara-cytidine 5'-(diethyl phosphoramidate) |

\| = $N^4$-trichloethoxycarbonyl-ara-cytidine 5'-phosphate
\|\| = DCC = dicyclohexylcarbodiimide Where the acryl radical attached to the 5'-oxygen of ara-cytidine is $$A_2O-\overset{\overset{S}{\|}}{\underset{OB_2}{P}}-,$$

the acylating agent is prepared in accordance with J. Am. Chem. Soc. 88, 4292 (1966), and with Angew. Chem. Internal. Edit. 6, 362 (1967), previously referred to in connection with Table VIII. In this class $A_2$ and $B_2$ have the meanings given above with respect to Table X. Representative compounds involved are:

TABLE XI $$\left(A_2O-\overset{\overset{S}{\|}}{\underset{OB_2}{P}}-\right)$$

| $A_2$ | $B_2$ | Acylating Agent | Final Product |
|---|---|---|---|
| H— | $C_2H_5$— | ethyl dichlorothiophosphate | ara-cytidine 5'-(o-ethylphosphorothioate) |
| $C_2H_5$— | $C_2H_5$— | diethyl dichlorothiophosphate | ara-cytidine 5'-(o,o-diethyl phosphorothioate) |
| H— | H— | triimidazolyl 1-phosphinsulfide | ara-cytidine 5'-phosphorothioate |

We have discovered a further method for the preparation of the 5'-esters described in this invention without resort to a special blocking group for the amino function. The alternate route takes advantage of the fact that when the amino group is protonated it is unreactive toward acylating agents. Thus, we simply use the proton as the blocking group, reacting a suitably activated acid, such as an acid chloride or anhydride, with an acid salt, such as the hydrochloride salt, of the nucleoside.

As an example, one equivalent of palmityl chloride is allowed to react at room temperature with a solution of ara-cytidine hydrochloride in dimethylacetamide or dimethylformamide. After a few hours, thin layer chromatography shows that the main product is 5'-O-palmityl ara-cytidine, with small amounts of diesterified products. The solvent is evaporated in vacuo, and the oil is converted to a solid by trituration with aqueous bicarbonate. The solid is collected on a filter and washed with water, pressed dry, and washed thoroughly with ethyl acetate to remove impurities. The resulting product, obtained in better than 50% yield, The method is applicable to all nucleosides bearing an amino group, such as nucleosides of adenine and guanine. The acyl moiety includes that of any acid that can be suitably activated, for example by the formation of an acid chloride, anhydride, or mixed anhydride, such that it can form an ester bond with an alkyl hydroxyl group but is unreactive towards a protonated amino group. The 5'-O-acyl derivatives of ara-cytidine described in the preceding discussions as made by the $N^4$-trihaloethoxycarbonyl-protected method, and illustrated in the above Tables I to XI, can also be made by the proton-protected route. The acylating agents used in the $N^4$-trihaloethoxycarbonyl-protected method and exemplified in Tables I to XI are applicable in the proton-protected route.

The proton-protected process is illustrated in Examples 24 to 32.

EXAMPLE 1

Preparation of $N^4$-trichloroethoxycarbonyl-5-O-trityl ara-cytidine

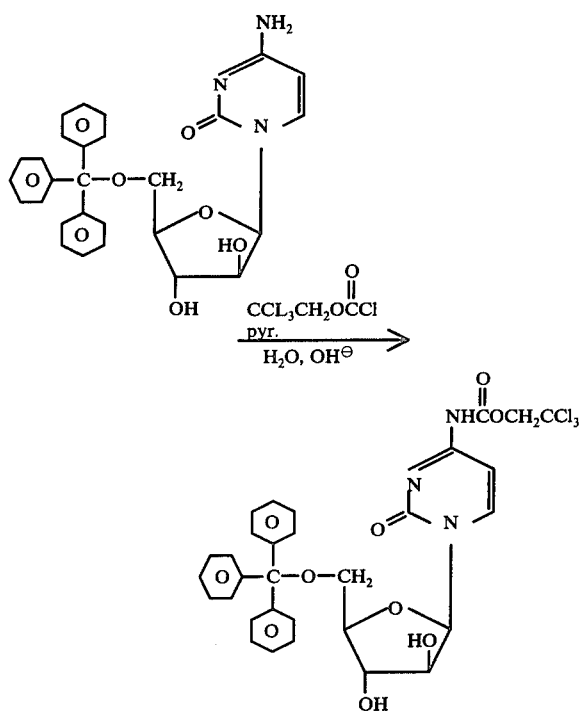

A 193.69 g. (.40M) sample of 5'-O-trityl ara-cytidine is dissolved in 4 l. of freshly distilled anhydrous pyridine. The solution is cooled to 3° and treated with 84.4 g. (.40M) of trichloroethoxycarbonyl chloride. The solution is stirred at 3° for 4 hours and then allowed to come to 25° over ca. 18 hours. The pyridine is distilled at 40° in vacuo and the gummy residue treated with 1 l. of methylene chloride. A solid (23.7 g.) separated and is removed by filtration. Thin layer chromatography (TLC) shows the material to be starting material. The methylene chloride solution is washed 3 times with 0.1 N hydrochloric acid and once with saturated salt solution. After drying over sodium sulfate the methylene chloride is allowed to slowly evaporate, whereupon crystals are deposited. The crystals are collected by filtration, washed with cold methylene chloride and dried giving 64.5 g. of desired product. TLC of the methylene chloride mother liquors show spots moving faster than the product which are probably materials acylated at 2' and 3' position. These are hydrolyzed by treating the mother liquor residue with 1 l. of tetrahydrofuran and 1 l. of 0.3 N sodium hydroxide. After 1.5 hours all the faster moving TLC spots have disappeared. The reaction is acidified to pH 6.5 with concentrated hydrochloric acid. The tetrahydrofuran is distilled in vacuo and the aqueous residue extracted with methylene chloride. The methylene chloride is washed and dried as above and again set out to evaporate. Again crystals are deposited. These are collected and washed giving 42.5 g. of product. The mother liquors are evaporated further and deposit another 45.5 g. of material which this time is about 50—50 product and starting material as seen by TLC. The 45.5 g. is heated with 500 ml. of acetone and the residual material removed by filtration. This is found to be trityl ara-cytidine. The acetone mother liquors are evaporated to dryness and crystallized from methylene chloride by slow evaporation giving 19 g. of product. The total yield is thus 126 g. of product or 48% of theory. A sample is prepared for analyses by crystallizing it twice from methylene chloride.

Anal. Calcd. for $C_{31}H_{28}Cl_3N_3O_7$:
C, 56.30; H, 4.27; Cl, 16.11; N, 6.36.
Found: C, 56.46; H, 4.30; Cl, 15.25; N, 7.26.
Ultraviolet Spectrum $[\lambda_{max}^{EtOH} m\mu \ (\epsilon \times 10^{-3})]$: 232 (11.8), 296 (5.38).

infrared Spectrum ($\gamma$ mull): 3380, 3200, 3120 sh. 1765, 1650, 1620, 1570, 1505, 1330, 1245, 1200, 1100 m, 1085, 1065, 810, 785, 770, 750, 740, 715 and 705.

EXAMPLE 2

Preparation of $N^4$-trichloroethoxycarbonyl ara-cytidine

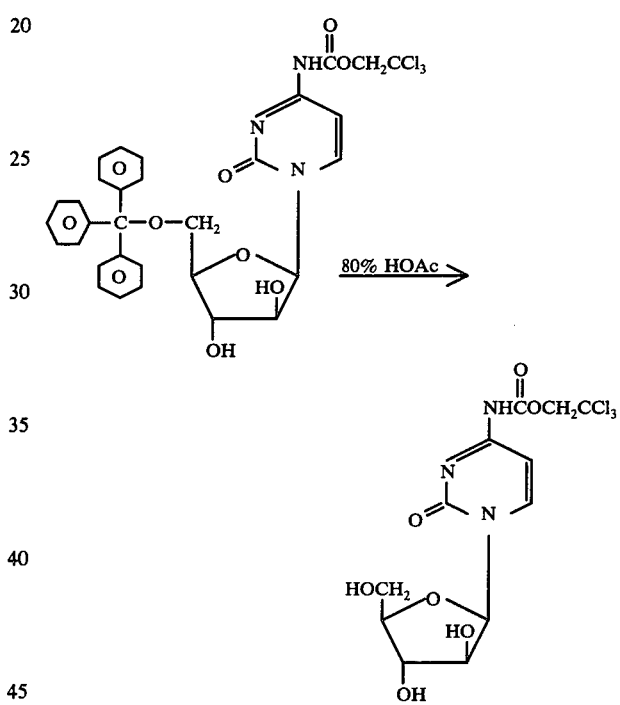

A 116.2 g. (.175 M) quantity of $N^4$-trichloroethoxycarbonyl-5'-O-trityl ara-cytidine is treated with 1 l. of 80% (V/V) acetic acid for 48 hours at 25°. The mixture deposits crystalline trityl containing material during this period which is removed by filtration. The filtrate is evaporated to dryness in vacuo and the last traces of acid removed by codistillation in vacuo with several portions of ethanol. The glassy residue is crystallized from ethanol giving 62.5 g. of product. These materials are found by NMR analysis to contain between 10 and 15% of triphenylmethylcarbinol and/or its ethyl ether. The compound is purified for analysis by chromatography on silica gel, eluting with cyclohexane-ethyl acetate-ethanol (5:3:1) and subsequent crystallization from methylene chloride.

Anal. Calcd. for $C_{12}H_{14}Cl_3N_3O_7$: C, 34.43; H, 3.37; Cl, 25.41; N, 10.04.
Found: C, 34.59; H, 3.61; Cl, 24.82; N, 9.99.
Infrared Spectrum ($\gamma_{cm^{-1}mull}$): 3400, 1765, 1640, 1575, 1510, 1330, 1275, 1235, 1195, 1120, 1105, 1070, 1055, 1035, 810, 745.

Ultraviolet Spectrum [$\lambda_{max}^{EtOH}$ ($\epsilon \times 10^{-3}$)]: 212 (21.8), 239 (14.5), 296 (8.3).

EXAMPLE 3

Preparation of 5'-O-pivaloyl-$N^4$-trichloroethoxycarbonyl ara-cytidine

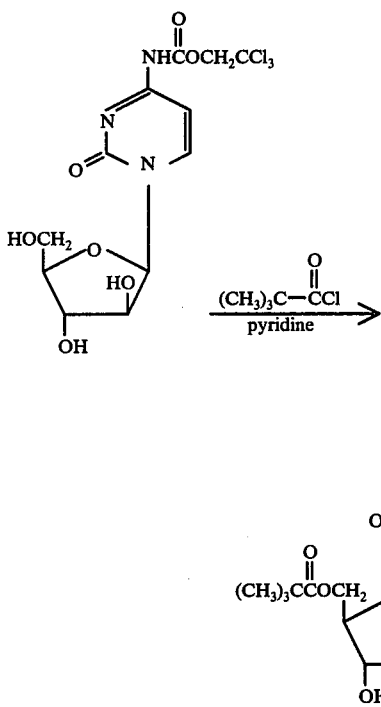

A 4.18 g. (10 millimole) sample of $N^4$-trichloroethoxycarbonyl ara-cytidine is dissolved in 50 ml. of freshly distilled anhydrous pyridine. The solution is treated dropwise with 1.32 g. (1.4 ml., 11 millimoles) of pivaloyl chloride in 10 ml. of pyridine at 25°. TLC [silica gel; cyclohexane-ethyl acetate-ethanol (5:3:1)] indicates the reaction has not progressed significantly after 48 hours. Thus, another 1.32 g. (11 millimoles) of pivaloyl chloride in 10 ml. pyridine is added and then reaction allowed to stand yet 24 hours longer. TLC indicates that little if any of the starting material remains. The reaction mixture is poured into 60 ml. of water and the mixture evaporated to dryness in vacuo. The last traces of pyridine are removed by codistillation several times with toluene in vacuo. The residue is dissolved in chloroform and washed with water, saturated sodium chloride and dried over sodium sulfate. The chloroform is distilled in vacuo and the residue crystallized from acetone giving 1.75 g. of product.

In place of pivaloyl chloride pivaloyl anhydride can be used as the pivaloylating agent in the above sample.

In place of pivaloyl chloride there can be substituted isobutyryl chloride or β-chloropivaloyl chloride, thus producing, respectively, 5'-O-isobutyryl-$N^4$-trichloroethoxycarbonyl ara-cytidine and 5'-O-β-chloropivaloyl-$N^4$-trichloroethoxycarbonyl ara-cytidine.

EXAMPLE 4

Preparation of 5'-O-pivaloyl ara-cytidine

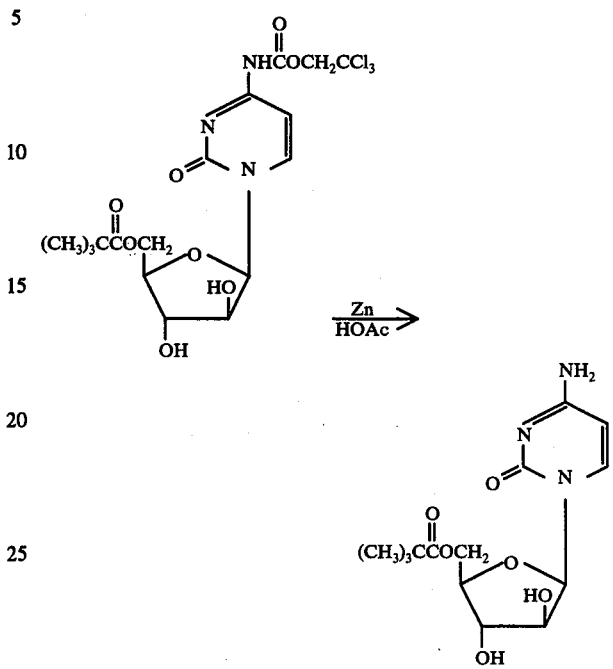

A 1.50 g. (3.0 millimole) sample of 5'-O-pivaloyl-$N^4$-trichloroethoxycarbonyl ara-cytidine is treated with 25 ml. of 90% (V/V) acetic acid and 2.0 g. (31 millimoles) of zinc dust and the mixture stirred ca. 18 hours at 25°. The reaction mixture is then filtered and the filtrate evaporated to dryness in vacuo. The residue is chromatographed on 200 g. of silica gel packed and eluted with cyclohexaneethyl acetate-ethanol (5:3:1). The first forty 100 ml. fractions contain none of the desired product, so a switch is made to the solvent system, methyl ethyl ketone-acetonewater (72:20:8). Fractions 1-18 are combined and evaporated to dryness. Crystallization of the residue from methanol gives 715 mg. of product, m.p. 255° (dec.). Like results are obtained substituting for the starting material, 5'-O-isobutyryl-$N^4$-trichloroethoxycarbonyl ara-cytidine and 5'-O-β-chloropivaloyl-$N^4$-trichloroethoxycarbonyl ara-cytidine producing, respectively, 5'-O-isobutyryl ara-cytidine and 5'-O-β-chloropivaloyl ara-cytidine.

In place of pivaloyl chloride in Example 3, benzoyl chloride can be substituted to provide 5'-O-benzoyl-$N^4$-trichloroethoxycarbonyl ara-cytidine which can be substituted in the process of Example 4 above to provide 5'-O-benzoyl ara-cytidine.

EXAMPLE 5

Preparation of 5'-O-benzoyl cytosine arabinoside hydrochloride

5'-O-benzoyl cytosine arabinoside (65 g.) is dissolved in 250 ml. methanol with the aid of 19 ml. concentrated hydrochloric acid. Ether (500 ml.) is added to opalescence. The hydrochloride rapidly crystallizes. It is collected, washed with methanol-ether (1:2), ether, and dried, weight 60.5 g., m.p. 204°-205° dec. Ether is added to the mother liquor to opalescence. The second crop is collected, washed with ether, and dried, weight 6.5 g. (total yield 67 g., 98.5%), m.p. 200°-201° dec.

EXAMPLE 6

Preparation of 5'-O-palmityl ara-cytidine

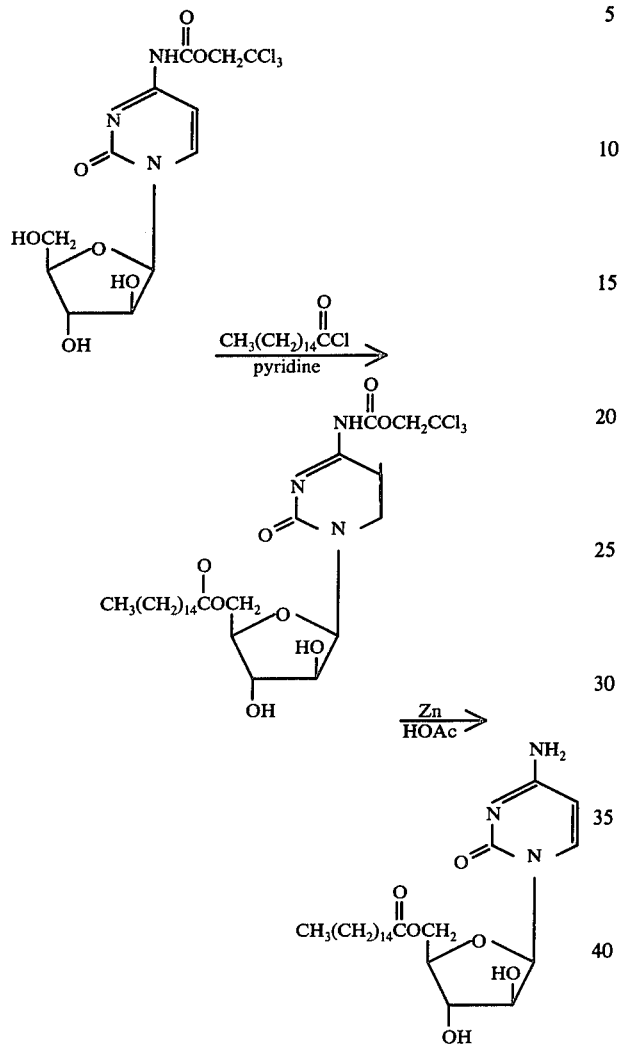

A 4.18 g. (10 millimoles) sample of N⁴-trichloroethoxycarbonyl ara-cytidine is dissolved in 50 ml. of anhydrous redistilled pyridine and treated dropwise at room temperature with 3.0 g. (11 millimoles) of palmityl chloride dissolved in 10 ml. of methylene chloride. After standing 18 hours 25°, the reaction mixture is poured into 60 ml. of water and the solvent distilled in vacuo until about 10 ml. remains. A semisolid separates and is obtained by decantation followed by washing with water. The resultant mass is crystallized from methanol giving 5.5 g. of material that is presumed to be 5'-O-palmityl-N⁴-trichloroethoxycarbonyl ara-cytidine on the basis of its conversion to the desired product. This material is dissolved in 100 ml. of 90% acetic acid and treated with 10 g. of zinc dust. The reaction is stirred for 6 hours at 25°. The zinc remaining is removed by filtration and the filtrate evaporated to dryness in vacuo. The last traces of acetic acid are removed by repeated codistillation in vacuo with ethanol. The residue is then chromatographed on 100 g. of silica gel, packed and eluted with cyclohexane-ethyl acetate-ethanol (5:3:1). After taking ten 100 ml. fractions, the solvent is switched to methyl ethyl ketone-acetone-water (72:20:8) and another ten 100 ml. fractions taken. Fractions 14–20 are combined and evaporated to dryness. The residue is crystallized from methanol giving 870 mg. of product, m.p. 139°–141°. A sample is submitted for analysis after two further crystallizations from methanol, m.p. 143°–146°.

Anal. Calcd. for $C_{25}H_{43}N_3O_6$: C, 62.34; H, 9.00; N, 8.72

Found: C, 62.86; H, 9.19; N, 8.47, 8.72.

Ultraviolet Spectrum $[\lambda_{max}^{EtOH} \, m\mu \, (\epsilon \times 10^{-3})]$: 273 (8.30).

Infrared Spectrum $(\gamma_{cm^{-1}}^{mull})$: 3430, 3330, 3280 sh, 1740, 1665 sh, 1635, 1600, 1535, 1495, 1485, 1290, 1255, 1195, 1175, 1110, 1095, 1040, 860, 790, 785, 780.

NMR Spectrum: Supports proposed structure.

EXAMPLE 7

Preparation of 5'-O-palmityl cytosine arabinoside hydrochloride

5'-palmityl cytosine arabinoside, 55 g. (0.114 mole) is dissolved in a mixture of 350 ml. methanol and 10.5 ml. concentrated hydrochloric acid. The solution is diluted with ether until crystallization ensues, and then further diluted to 4 liters with ether. The crystalline hydrochloride is collected, washed with ether, and dried. Yield 53.8 g. (91%), m.p. 180°–182°.*

* Using sulfuric, phosporic, glutamic, dihydroxytartaric, trihydroxybenzoic or formic in the above procedure results in the corresponding salt.

EXAMPLE 8

Preparation of 5'-O-octanoyl ara-cytidine

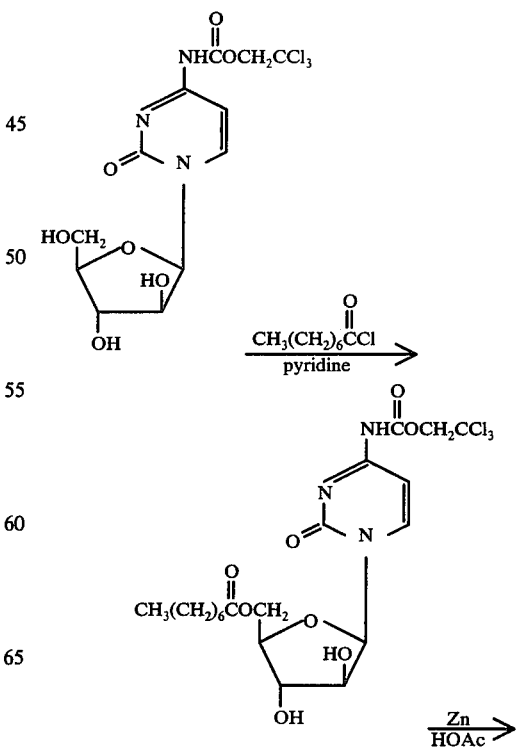

-continued

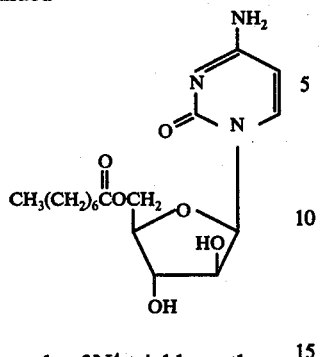

A 4.18 g. (10 millimoles) sample of N⁴-trichloroethoxycarbonyl ara-cytidine is dissolved in 50 ml. of anhydrous redistilled pyridine and resultant solution treated dropwise with a solution of 1.8 g. (11 millimoles) of octanoyl chloride in 10 ml. of methylene chloride. The reaction mixture is stirred for 18 hours at room temperature and then poured into 60 ml. of water. The solvent is reduced in volume to about 10 ml. by distillation in vacuo. The mother liquors are decanted from the solid which separates. The solid is washed with water, filtered, dried and crystallized from methanol giving 3.5 g. of 5'-O-octanoyl-N⁴-trichloroethoxycarbonyl ara-cytidine. This material is dissolved in 50 ml. of 90% acetic acid and the solution is treated with 5 g. of zinc dust. After the reaction mixture has shaken 5 hours at 25°, the residue zinc solids are removed by filtration and the filtrate evaporated to dryness in vacuo. The last traces of acetic acid are removed by redistillation in vacuo with several portions of ethanol. The residue is chromatographed on 100 g. of silica gel, packed and eluted with methyl ethyl ketone-acetone-water (72:20:8). Fractions of 100 ml. volume are collected. Fractions 4–8 are combined and evaporated to dryness. The residue is crystallized from methanol giving 1.2 g. of product, m.p. 161.5°–162.5°. A sample is submitted for analyses after another crystallization from aqueous methanol, m.p. 124°–125°. The melting point change apparently reflects a change in the state of hydration or change in crystal structure since TLC indicates the material to be unchanged.

Anal. Calcd. for $C_{17}H_{27}N_3O_6 \cdot H_2O$: C, 52.69; H, 7.55; N, 10.85

Found: C, 52.81; H, 7..97; N, 11.32.

Ultraviolet Spectrum $[\lambda_{max}^{EtOH} \, m\mu \, (\epsilon \times 10^{-3})]$: 274 (8.15).

Infrared Spectrum $(\gamma_{cm^{-1}}^{mull})$: 3530, 3480, 3450, 3390, 3320, 3280, 3210, 1725, 1710, 1655, 1630, 1530, 1490, 1280, 1240, 1195, 1175, 1130, 1115, 1100, 1090, 1050, 1040, 810, 780.

NMR Spectrum: Supports proposed structure.

The procedures of Examples 5–6 can be followed, substituting stearyl chloride and oleyl chloride for the acylating agents of the examples, producing, respectively, 5'-O-stearyl ara-cytidine and 5'-O-oleyl ara-cytidine.

EXAMPLE 9

Preparation of 5'-O-acetyl ara-cytidine

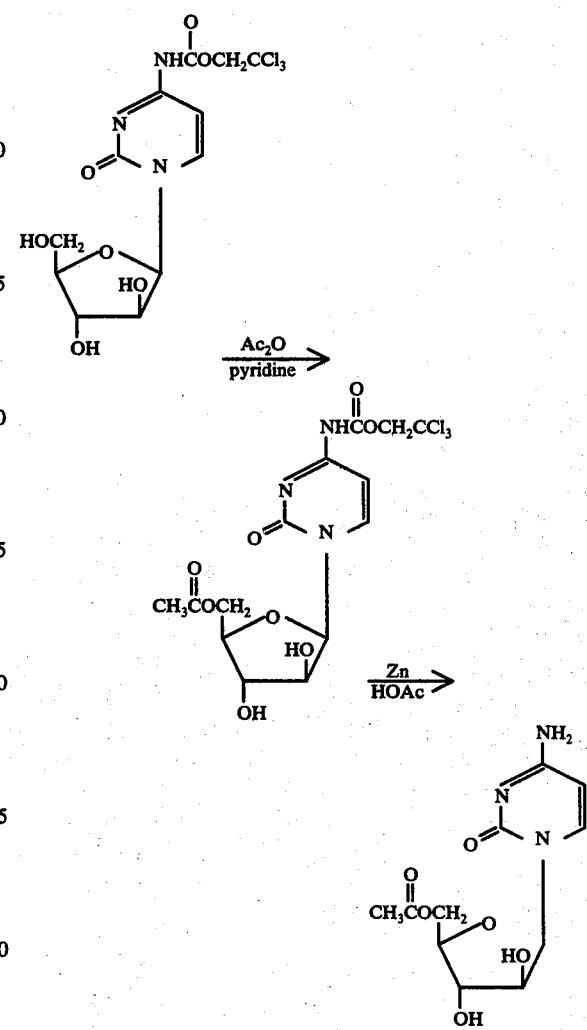

A 4.18 g. (10 millimoles) sample of N⁴-trichloroethoxycarbonyl ara-cytidine is dissolved in 50 ml. of anhydrous freshly distilled pyridine. The resultant solution is treated dropwise with 1.03 g. (10 millimoles) of acetic anhydride. The reaction mixture is stirred at 25° for 18 hours, then poured into 60 ml. of water and evaporated to dryness. The residue is chromatographed on 100 g. of silica gel and eluted with cyclohexane-ethyl acetate-ethanol (5:3:1). The fractions containing the material with an Rf only slightly faster than the starting material are combined and evaporated to dryness. Crystallization of the residue gives 1.05 g. of material presumed to be 5-O-acetyl-N⁴-trichloroethoxycarbonyl ara-cytidine on the basis of its subsequent conversion to 5'-O-acetyl ara-cytidine. This material is dissolved in 50 ml. of 90% (V/V) acetic acid and the solution treated with 1.0 g. of zinc dust. The reaction mixture is shaken for 6 hours at 25°. The zinc solids remaining are then removed by filtration and the fitrate evaporated to dryness in vacuo. The residual gum is freed from traces of acetic acid by codistillation in vacuo with several portions of ethanol. The residue is chromatographed on 100 g. of silica gel, packed and eluted with cyclohexaneethyl acetate-ethanol (5:3:1). The solvent is switched to methyl ethyl ketone-acetone-water (72:20:8). The fractions containing the desired product are combined and evaporated to dryness. The material is thus rechromatographed on 50 g. of silica gel as described above. The fraction from this column containing the desired material are combined and evaporated to dryness. The residue is crystallized from aqueous methanol-benzene giving 300 mg. of product, m.p. 115°-117.5°.

Anal. Calcd. for $C_{11}H_{15}N_3O_6 \cdot \frac{1}{2}H_2O$: C, 44.90; H, 5.48; N, 14.28.

Found: C, 45.13; H, 5.95; N, 14.55.

Ultraviolet Spectrum $[\lambda_{max}^{etOH} m\mu\ (\epsilon \times 10^{-3})]$: 273 (8.65).

Infrared Spectrum $(\gamma_{cm-1}^{mull})$: 3400, 3340, 3210, 1745, 1660 sh, 1640, 1610, 1535, 1490, 1280, 1255 sh, 1245, 1230, 1105, 1080, 1070, 1050, 810, 780, 690.

NMR Spectrum: Suports proposed structure.

EXAMPLE 10

Preparation of 5'-O-(2,4,6-trimethylbenzoyl) ara-cytidine.

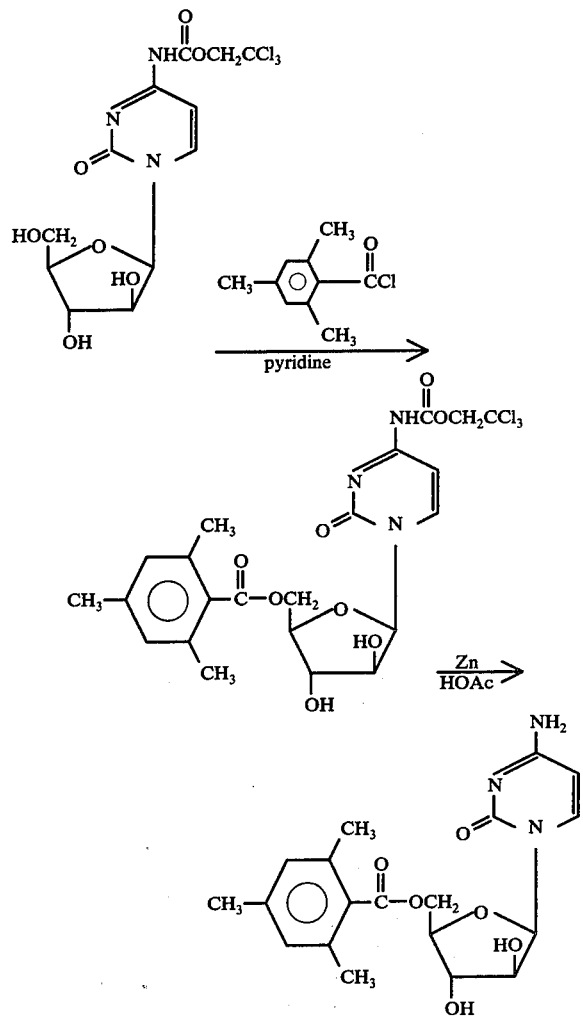

A 4.18 g. (10 millimoles) sample of N⁴-trichloroethoxycarbonyl ara-cytidine is dissolved in 50 ml. of anhydrous redistilled pyridine and the resultant solution treated dropwise with 2.0 g. (11 millimoles) of 2,4,6-trimethylbenzoyl chloride dissolved in 10 ml. of methylene chloride. After 3 days at 25°, TLC indicates that starting material is still present. Thus, another 2.0 g. of 2,4,6-trimethylbenzoyl chloride is added and the reaction allowed to stand another 24 hours at 25°. The reaction mixture is then poured into water and evaporated to dryness in vacuo. Th residue is chromatographed on 100 g. of silica gel. The product is eluted with methanol-benzene (5:95). The fractions containing the material with Rf only slightly faster than the starting material are combined and evaporated to dryness. The residue is crystallized from methanol giving 2.0 g. of material presumed to be N⁴-trichloroethoxycarbonyl-5'-O-(2,4,6-trimethylbenzoyl) ara-cytidine on the basis of its conversion to 5'-O-trimethylbenzoyl ara-cytidine, m.p. 122°-125° (dec.). This material is dissolved in 50 ml. of 90% (V/V) acetic acid. The solution is treated with 2 g. of zinc dust and shaken for 6 hours. The zinc containing solids are filtered from the reacting mixture and the filtrate evaporated to dryness in vacuo. The residue is chromatographed on 100 g. of silica gel, eluting with mixtures of methanol benzene (5:95) to pure methanol. The desired material is found in the methanol fractions, which are then combined and evaporated to dryness. The residue is crystallized from methanol giving 670 mg. of 5'-O-(2,4,6-trimethylbenzoyl) ara-cytidine, m.p. 252°-253° (dec.). A sample crystallized once more from methanol is submitted for analysis, m.p. 255°-256° (dec.).

Anal. Calcd. for $C_{19}H_{13}N_3O_6 \cdot \frac{1}{2}H_2O$: C, 57.28; H, 6.07; N, 10.55.

Found: C, 57.15; H, 6.34; N, 10.86.

Ultraviolet Spectrum $[\lambda_{max}^{EtOH} m_\mu(\epsilon \times 10^{-3})]$: 273 (9.40).

Infrared Spectrum $(\gamma_{cm-1}^{mull})$: 3430 sh, 3400, 3340, 3280, 3210, 3120, 1720, 1695, 1655, 1635, 1625, 1535, 1490, 1285, 1175, 1120, 1115, 1095, 1070, 1055, 810, and 780.

NMR Spectrum: Supports proposed structure.

The use as acylating agent of p-nitrobenzoyl chloride, o-toluoyl chloride, benzoyl chloride, 2,6-dimethylbenzoyl chloride, 2,4,6-trimethylbenzoyl chloride, 1-fluorene carbonyl chloride, p-anisoyl chloride, 3,4,5-trimethoxybenzoyl chloride, p-toluoyl chloride, cyclohexane carbonyl chloride, picolinyl chloride or 2-thiophene carbonyl chloride produces, respectively, 5'O-p-nitrobenzoyl ara-cytidine, 5'O-toluoyl ara-cytidine, 5'O-benzoyl ara-cytidine, 5'O-2,6-dimethylbenzoyl ara-cytidine, 5'-O-2,4,6-trimethylbenzoyl ara-cytidine, 5'-O-1-fluorene carbonyl ara-cytidine, 5'-O-p-anisoyl ara-cytidine, 5'-O-3,4,5-trimethoxybenzoyl ara-cytidine, 5'O-p-toluoyl ara-cytidine, 5'O-cyclohexane carbonyl ara-cytidine, 5'-O-picolinyl ara-cytidine, and 5'-O-2-thiophene carbonyl ara-cytidine.

EXAMPLE 11

Preparation of 5'-O-adamantoyl ara-cytidine

5'-O-Trityl ara-cytidine (2.42 g., 5.0 millimoles) is dissolved in 50 ml. of redistilled pyridine and cooled in a dri ice-acetone bath until a slurry formed. The slurry is treated with β,β,β-trichloroethoxycarbonyl (TCEC) chloride (3.2 g., 15 millimoles). The mixture is agitated thoroughly and then allowed to stand at 0° for 20 hours. The reaction is warmed to 25° and maintained at that temperature for 4 hours. The pyridine is distilled at a temperature below 40° on a rotary evaporator. The residual gum is dissolved in 100 ml. of methylene chloride and washed 4 times with 1 N hydrochloric acid. The methylene chloride layer is dried ($Na_2SO_4$) and distilled. The residual gum is treated with 200 ml. of 1% trifluoroacetic acid in chloroform for 2 hours at 25° to remove the trityl group. The chloroform solution is evaporated to dryness and the gum dissolved in pyridine and treated with adamantane-1-carboxylic acid chloride (1-adamantane carbonyl chloride) (1.0 g., 5mM). The solution is warmed to 50° and maintained at that temperature for 24 hours. The pyridine is distilled on a rotary evaporator and the residue dissolved in 100 ml. of chloroform. The chloroform solution is washed with 200 ml. of water, 200 ml. of 4% sodium bicarbonate and twice with 200 ml. of water. The chloroform solution is dried (Na$_2$SO$_4$) and distilled on a rotary evaporator. The residue is dissolved in 25 ml. of 90% acetic acid to which is added 2 g. of zinc dust. After standing 2 hours at room temperature the mixture is filtered and the filtrate distilled. The residue is dissolved in a minimum amount of chloroform and absorbed onto a 300 g. column of silica gel. The desired product is eluted with chloroform-methanol-acetic acid (80:20:1). The material is crystallized from methanol, giving 250 mg. of product.

EXAMPLE 12

Preparation of 5'-O-adamantoyl cytosine arabinoside hydrochloride

5'-O-adamantoyl cytosine arabinoside (42 g.) is suspended in 400 ml. methanol, and 12.5 ml. of concentrated hydrochloric acid is aded to dissolve the material. Crystallization rapidly ensues and the mixture is diluted to one liter with ether. The crystalline product is collected, washed with ether and dried, weight 32.9 g., m.p. 246° dec. The mother liquor is concentrated and a second crop obtained, weight 3.5 g., m.p. 241° dec. (total yield = 36.4 g., 79%).

Substituting, as acylating agent, 1-norbornane carbonyl chloride, 2-adamantane carbonyl chloride, 1-adamantaneacetyl chloride, α-chloro-3,5,7-trimethyl-1-adamantane acetyl chloride and 2-quinuclidine carbonyl chloride produces, respectively, 1-norbornane carbonyl ara-cytidine, 5'-O-2-adamantane carbonyl ara-cytidine, 5'-O-1-adamantane acetyl ara-cytidine, 5'-O-α-chloro-3,5,7-trimethyl-1-adamantane ara-cytidine, and 5'-O-2-quinuclidine carbonyl ara-cytidine.

EXAMPLE 13

Preparation of 5'-O-(p-toluenesulfonyl) ara-cytidine

A 4.18 g. (10 millimoles) sample of N$^4$-trichloroethoxycarbonyl ara-cytidine is dissolved in 50 ml. of freshly distilled anhydrous pyridine. The solution is treated dropwise with 2.85 g. of p-toluenesulfonyl chloride (15 millimoles) dissolved in 10 ml. of pyridine. The reaction mixture is allowed to stir at room temperature over the weekend, and then is poured into 60 ml. of water and taken to dryness at 50° on a rotary evaporator. The crude gum is then dissolved in 50 ml. of methanol and 5 g. of zinc dust added. The reaction mixture is then heated to boiling for 15 minutes. TLC is checked and shows no starting material left. The zinc is filtered and the preparation taken to dryness. Th residue is then absorbed onto a 200 g. column of silica gel made up with cyclohexane, ethyl acetate, 95% EtOH (5:3:1). The column is eluted with 1 l. of this same solvent. This elutes only faster moving material which is discarded. The column is then eluted with 15, 100 ml. fractions of MEK*. acetone, H$_2$O (72:20:8). Fractions 5–10 contain what appears to be the desired product. These fractions move a little slower than the starting material on TLC. and are combined and crystallized from methanol. Yield 950 mg., m.p. 158°–168° (dec. at 195°). A sample is recrystallized from methanol for analysis, m.p. 171°–174°.

*Methyl ethyl ketone

Anal. Calcd. for C$_{16}$H$_{19}$O$_7$N$_3$S: C, 48.36; H, 4.82; N, 10.57; S, 8.04.

Found: C, 48.46; H, 5.25; N, 10.49; S, 8.13.

Ultraviolet Spectrum [$\lambda_{max}^{EtOH}$ ($\epsilon \times 10^{-3}$)]: 224 (19.7); 269 sh (8.60); 273 (8.95).

Infrared Spectrum [$\gamma_{cm^{-1}}^{mull}$]: 3480, 3330 sh, 3280 sh. 3240 sh, 3210 sh, 1650, 1615, 1560 w, 1535, 1500, 1360, 1355, 1290, 1195, 1175, 1070, 1040, 980, 835, 820, 800, 785, 665.

Infrared spectrum is proper for the sulfonate.

EXAMPLE 14

Preparation of 5'-O-cyclobutyl carbonyl ara-cytidine

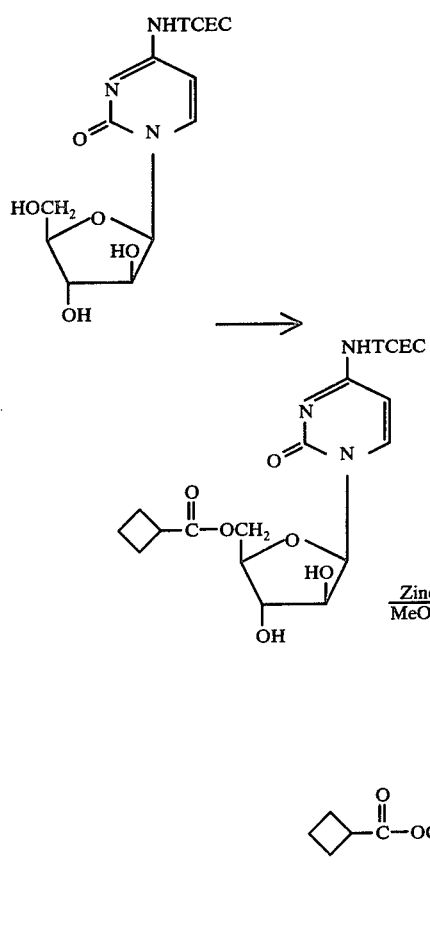

A 8.36 g. (20 millimoles) sample of N⁴-trichloroethoxycarbonyl ara-cytidine is dissolved in 50 ml. of freshly distilled anhydrous pyridine. The solution is treated dropwise at room temperature with stirring with 4.0 g. (about 22 millimoles) of cyclobutanecarboxylic acid anhydride in 10 ml. of $CH_2Cl_2$. The reaction mixture is allowed to stir at room temperature overnight and a TLC plate is run on the crude reaction in the morning. TLC still shows some starting material left, so the preparation is heated to 50° in a water bath for 3 hours. TLC is unchanged so the reaction mixture is poured into 30 ml. of water and taken to dryness at 50° on the rotry evaporator. The residue is then dissolved in $CH_2Cl_2$ and washed once with saturated bicarbonate, twice with water. At this point, there is a lot of precipitate in the $CH_2Cl_2$ layer. This is filtered and washed with a small amount of $CH_2Cl_2$. Yield 3.4 g. This material has one major spot with a trace of the slower moving starting material. The $CH_2Cl_2$ solution (the mother liquors) contain 3 faster moving spots plus a trace of the crystalline solid plus the starting material. The 3.4 g. of crystalline solid is dissolved in 100 ml. of methanol and heated to boiling with 3.5 g. of zinc dust for 10 minutes on the steam bath. TLC shows no starting material left at this point. The zinc is filtered off and the methanol solution taken to dryness at 50° on the rotary evaporator. The clear residue is then absorbed onto a 200 g. column of silica gel made up with MEK, acetone and $H_2O$ (72:20:8) and the column eluted with 15, 50 ml. fractions of the same solvent. Based on TLC results, fractions 9–13 are combined and recrystallized from acetone. Yield 1.045 g. Recrystallized from acetone for analysis, a sample has a m.p. 200.0°–200.5°. TLC is the same as the first crop material.

Anal. Calcd. for $C_{14}H_{17}O_6N_3$: C, 51.68; H, 5.89; N, 12.92.

Found: C, 51.29; H, 6.13; N, 13.25.

Ultraviolet Spectrum $[\lambda_{max}^{EtOh} (\epsilon \times 15^{-3})]$: 230 sh (7.90); 273 (9.00).

Infrared Spectrum $[\gamma_{cm-1}^{mull}]$: 3440, 3330, 3260, 3210, 1700, 1655, 1635, 1600, 1525, 1295, 1255, 1185, 1135, 1105, 1050, 810.

Ultraviolet spectrum, infrared spectrum and NMR are proper for the proposed structure.

EXAMPLE 15

Preparation of 5'-O-(p-anisoyl) ara-cytidine

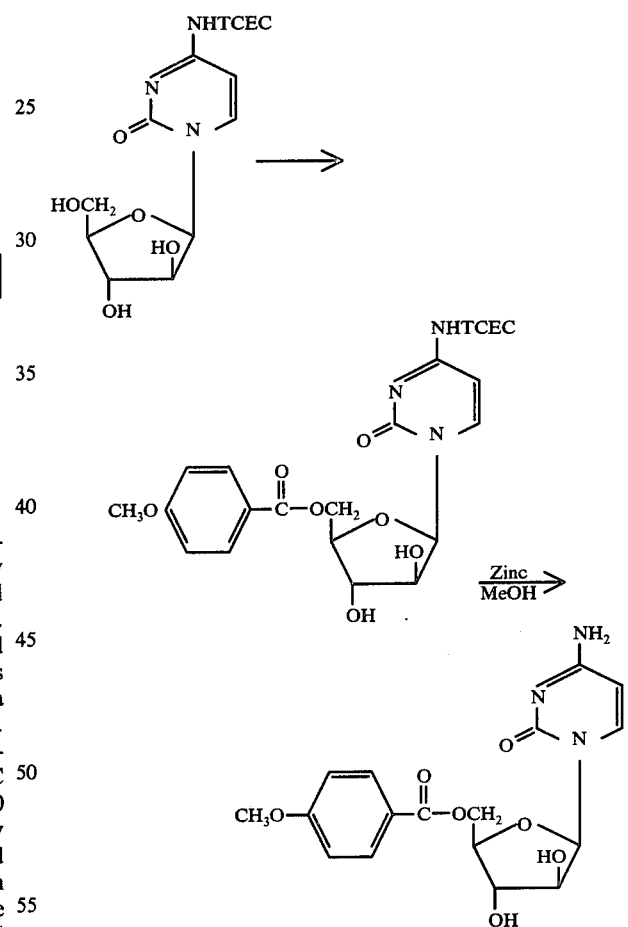

A 8.36 g. (20 millimoles) sample of N⁴-trichloroethoxycarbonyl ara-cytidine is dissolved in 50 ml. of freshly distilled anhydrous pyridine. The solution is treated dropwise with stirring at room temperature with 3.75 g. (22 millimoles) of anisoyl chloride in 10 ml. of $CH_2Cl_2$. The reaction mixture is allowed to stir at room temperature overnight and a TLC plate is run on the crude mixture in the morning. TLC still shows some starting material left. The preparation is heated to 50° in a water bath for 3 hours. TLC is unchanged so the reaction mixture is poured into 30 ml. of water and taken to dryness at 50° on a rotary evaporator. The residue is dissolved in CH₂Cl₂ and washed once with 100 ml. of saturated bicarbonate, once with H₂O and dried over sodium sulfate. The CH₂Cl₂ solution is then absorbed onto a 200 g. column of silica gel and eluted with 20, 50 ml. fractions of cyclohexane, ethyl acetate, 95% EtOH (5:3:1). Based on TLC results, fractions 10–18 are combined in methanol (100 ml.) and treated with 4 g. of zinc dust for 15 minutes at reflux on the steam bath. TLC at this point shows no starting material left so the solution is filtered free of zinc and the preparation taken to dryness on the rotary evaporator. The residue is then absorbed onto a 200 g. column of silica gel made up with MEK, acetone. H₂O and eluted with 20, 50 ml. fractions of the same solvent. Based on TLC results, fractions 10–16 are combined and recrystallized from methanol. Yield 795 mg., m.p. 225°–227° (dec.). Recrystallized from methanol a sample for analysis has m.p. 225°–227° (dec.).

Anal. Calcd. for $C_{17}H_{19}O_7N_3$: C, 54.11; H, 5.08; N, 11.14.

Found: C, 53.95; H, 4.81; N, 11.09.

Ultraviolet Spectrum $[\lambda_{max}^{EtOH} (\epsilon \times 10^{-3})]$: 258 (14.50); 271 sl sh (19.20); 278 sl sh (13.00); 283 sl sh (4.90).

The shift in the main absorption is due to the

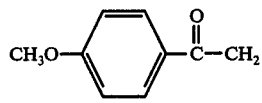

group as the 278 and 283 sl sh's. Ultraviolet spectrum supports the proposed structure.

Infrared Spectrum $[\gamma_{cm^{-1}}^{mull}]$: 3420, 3310, 1720, 1665, 1630, 1600, 1530, 1510, 1490, 1275, 1250, 1170, 1100, 1035, 850, 825, 790, and 770.

NMR and infrared spectrum are proper for the proposed structure.

EXAMPLE 16

Preparation of 5'-O-cyclohexyl carbonyl ara-cytidine

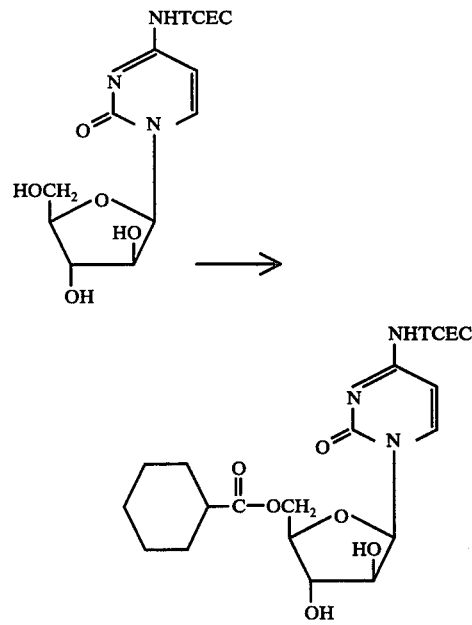

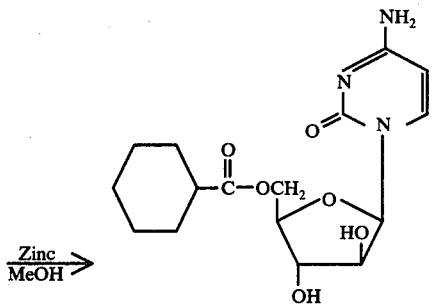

A 8.36 g. (20 millimoles) sample of N⁴-trichloroethoxycarbonyl ara-cytidine is dissolved in 50 ml. of freshly distilled anhydrous pyridine. The solution is treated dropwise with stirring and at room temperature with 3.22 g. (about 22 millimoles) of cyclohexanecarboxylic chloride in 10 ml. of CH₂Cl₂. The chloride is made by refluxing cyclohexanecarboxylic acid in thionyl chloride, removing the thionyl chloride on the rotary evaporator and distilling the chloride, boiling point 180°–181°. The reaction mixture is allowed to stir at room temperature overnight. A TLC is run on the crude mixture in the morning. The TLC still shows some starting material left so the preparation is heated to 50° in a water bath for 3 hours. The reaction mixture is poured into 30 ml. of water and taken to dryness at 50° on the rotary evaporator. The residue is then absorbed onto a 200 g. column of silica gel. and eluted with 25, 50 ml. fractions of cyclohexane, ethylacetate, 95% EtOH (5:3:1). The column is made up with the same solvent. TLC's are run on fractions 5–14 and on fraction 23. Based on TLC results, fractions 6–11 are combined. 3.387 g. in 100 ml. of methanol is treated with 4 g. of zinc dust at reflux for 15 minutes. TLC shows no starting material left at this point. The zinc is filtered off and the filtrate taken to dryness at 50° on the rotary evaporator. The residue is then absorbed onto a 200 g. column of silica gel made up with MEK, acetone, H₂O (72:20:8) and eluted with 20, 50 ml. fractions of the same solvent. Based on TLC results, fractions 10–14 are combined and recrystallized from methanol-acetone. Yield 1.384 g., m.p. sinters at 206° dec. at 229° (one spot by TLC). Recrystallized 100 mg. from the same solvent, a sample for analysis sinters about 210° and dec. at 231°.

Anal. Calcd. for $C_{16}H_{23}O_6N_3 \cdot \frac{1}{2}H_2O$: C, 53.03; H, 6.68; N, 11.60

Found: C, 52.85; H, 6.66; N, 11.95

Ultraviolet Spectrum $[\lambda_{max}^{EtOH} (\epsilon \times 10^{-3})]$: 315 sl sh (10.20); 230 sh (7.65); 273 (8.75).

Infrared Spectrum $[\gamma_{cm^{-1}}^{mull}]$: 3420, 3340, 3210, 1735, 1715, 1655, 1640, 1625, 1530, 1490, 1285, 1245, 1200, 1180, 1110, 1095, 1055, 815, and 780.

Ultraviolet spectrum supports the proposed structure.

NMR and infrared spectrum are proper for the proposed structure.

EXAMPLE 17

Preparation of 5′-O-β-chloropivaloyl ara-cytidine

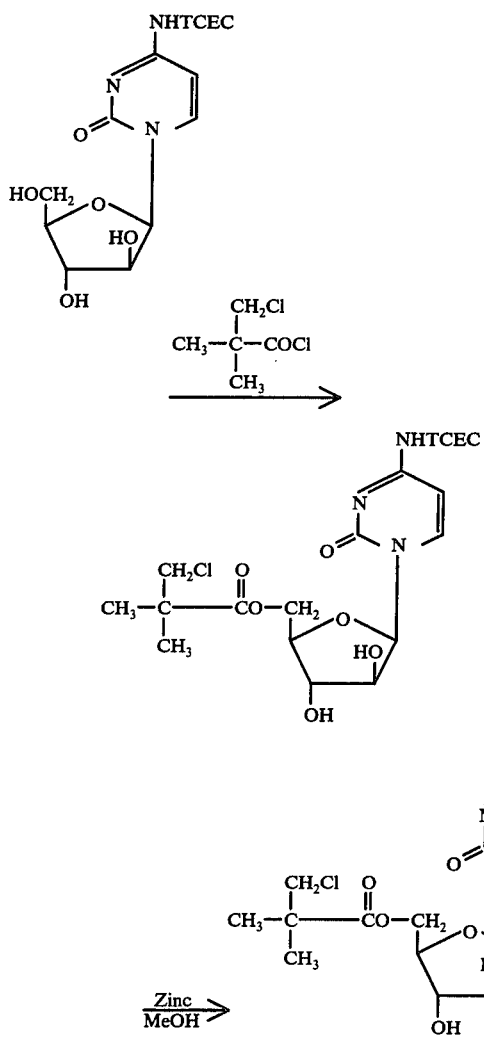

A 8.36 g. (20 millimoles) sample of $N^4$-trichloroethoxycarbonyl ara-cytidine is dissolved in 50 ml. of freshly distilled anhydrous pyridine. The solution is treated dropwise with stirring at room temperature with 3.4 g. (about 22 millimoles) of β-chloropivalic acid chloride. The chloride is made by refluxing β-chloropivalic acid (Aldrich) in an excess of thionyl chloride, distilling off the thionyl chloride, then the acid chloride, b.p. 158°–160°. After 18 hours at room temperature there is still starting material left by TLC. Another 3.4 g. of the acid chloride is added in 10 ml. of $CH_2Cl_2$. After 4 hours at room temperature the TLC is still mostly unchanged. The reaction mixture is warmed on the steam bath for 5–10 minutes. TLC at this point shows only a trace of the starting material. The preparation is poured into 60 ml. of water and taken to dryness on the rotary evaporator at 50°. The residue is then absorbed into a 200 g. column of silica gel made up with cyclohexane, ethyl acetate, 95% EtOH (5:3:1) and eluted with 20, 50 ml. fractions of the same solvent. Fractions 6–20 are slurried in a small amount of methanol and filtered and washed with 10–15 ml. of cold methanol. This material has one major spot by TLC with a trace of faster moving material and a trace of the starting material. Yield is 6.85 g. This material is dissolved in 100 ml. of methanol and heated to reflux with 7 g. of zinc dust for 15 minutes. TLC shows no starting material left so the zinc was filtered off, washed with methanol and the filtrate taken to dryness at 50° on the rotary evaporator. The residue is absorbed onto a 200 g. column of silica gel and eluted with 25, 50 ml. fractions of MEK, acetone, $H_2O$ (72:20:8). TLC's are run on crystalline fractions 11, 15 and 21. Based on TLC results, fractions 11–21 are combined and recrystallized from methanol. The compound will crystallize from $H_2O$ also. Yield 2.50 g., m.p. 238°–40° dec. A sample recrystallized for analysis from the same solvent has m.p. 238°–40° dec. One spot by TLC.

Anal. Calcd. for $C_{14}H_{20}O_6N_3Cl$: C, 46.48; H, 5.57; N, 11.61; Cl, 9.80

Found: C, 46.42; H, 5.68; N, 11.46; Cl, 10.16.

Ultraviolet Spectrum $[\lambda_{max}^{EtOH}(\epsilon \times 10^{-3})]$: 216 sl sh (10.20); 229 sh (7.90); 273 (9.05).

Infrared Spectrum $[\gamma_{cm^{-1}}^{mull}]$: 3410, 3440, 3340, 3260, 3220, 1710, 1655, 1635, 1600, 1565, 1525, 1485, 1300, 1255, 1190, 1125, 1100, 1055, and 810.

EXAMPLE 18

Preparation of ara-cytidine 5′-methyl carbonate

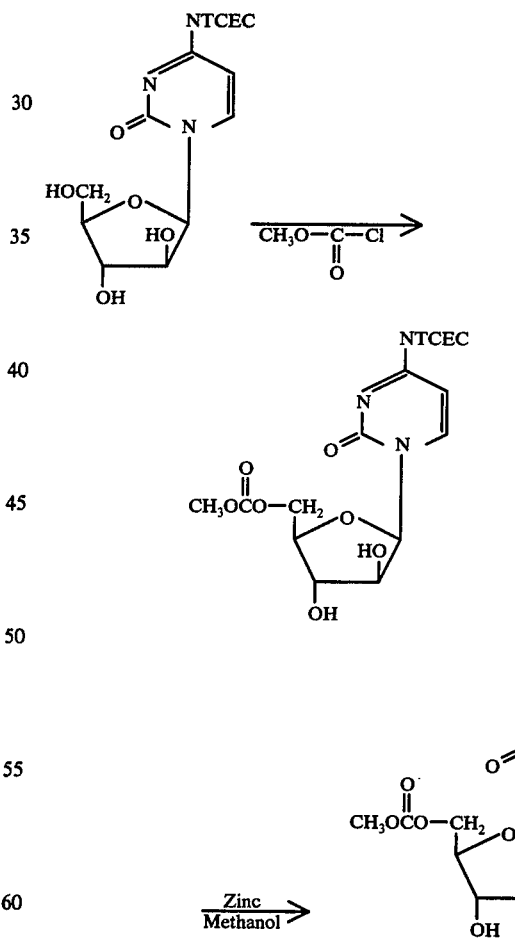

A 4.18 g. (10 millimoles) sample of $N^4$-trichloroethoxycarbonyl ara-cytidine is dissolved in 25 ml. of freshly distilled anhydrous pyridine. The solution is treated dropwise at room temperature with 1.0 g. of methyl chloroformate (about 22 millimoles) dissolved in 10 ml. of $CH_2Cl_2$. The solution is allowed to stir at room temperature overnight and the TLC is checked in the morning. TLC showed some starting material left. The preparation is taken to dryness at 50° on the rotary evaporator and the residue absorbed onto a 150 g. column of silica gel made up with cyclohexane, ethyl acetate, 95% EtOH (5:3:1). The column is eluted with 20, 50 ml. fractions of the same solvent. TLC's of fractions 9–17 shows fractions 10–13 to contain the desired

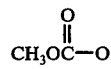

derivative of $N^4$-trichloroethoxycarbonyl ara-cytidine. These fractions of 2.465 g. are combined in 50 ml. of methanol and treated at reflux for 15 minutes on the steam bath with 3 g. of zinc dust. TLC shows no starting material left. The zinc is then filtered and the preparation taken to dryness on the rotary evaporator. The residue is then absorbed onto a 150 g. column of silica gel made up with MEK, acetone, methanol (5:2:3) and eluted with 25, 50 ml. fractions of the same solvent. TLC's are run on fractions 17–22 and based on the TLC results, fractions 19–22 are combined and recrystallized from methanol. Yield is 390 mg., m.p. 188.5°–90° dec. (foamed up the tube).

Anal. Calcd. for $C_{11}H_{15}O_7N_3$: C, 43.85; H, 5.02; N, 13.95. Found: C, 44.16; H, 5.26; N, 13.64.

Ultraviolet Spectrum $[\lambda_{max}^{EtOH}(\epsilon \times 10^{-3})]$: 215 sl sh (10.35); 230 (8.00); 273 (9.15).

Infrared Spectrum $[\lambda_{cm-1}^{mull}]$: 3460, 3340, 3250, 3230, 3180, 1765, 1640, 1625, 1560, 1530, 1500, 1315, 1280, 1090, 1070, 1035, 990 and 780.

Ultraviolet spectrum, infrared spectrum and NMR are all proper for the proposed structure.

EXAMPLE 19

Preparation of 5'-O-(p-nitrobenzoyl) ara-cytidine

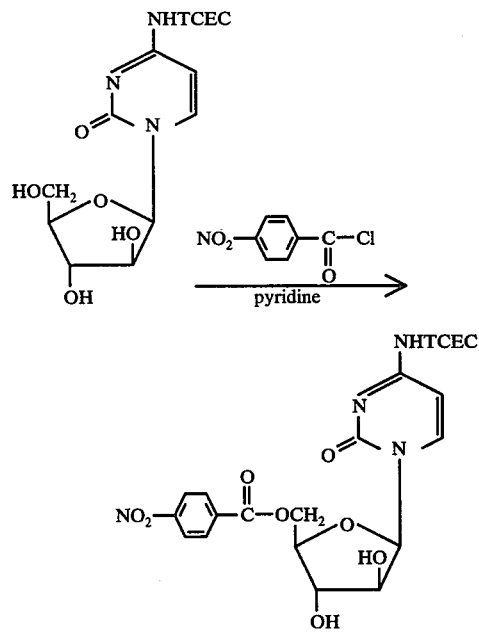

-continued

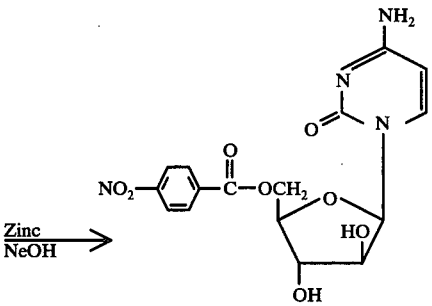

A 8.36 g. (20 millimoles) sample of $N^4$-trichloroethoxycarbonyl ara-cytidine is dissolved in 25 ml. of freshly distilled anhydrous pyridine. The solution is treated dropwise with 4.08 g. (about 22 millimoles) of p-nitrobenzoyl chloride dissolved in 25 ml. of the freshly distilled anhydrous pyridine. The solution is allowed to stir overnight at room temperature. TLC in the morning shows only a small amount of starting material left. The reaction mixture is poured into 25 ml. of water and taken to dryness at 50° on the rotary evaporator. The residue is absorbed onto a 200 g. column of silica gel made up with cyclohexane, ethyl acetate, 95% ethanol and eluted with 20, 50 ml. fractions of the same solvent. Fractions 7–16 are combined after TLC's are run on the fractions, slurried in methanol, the crystalline solid filtered and washed with a small amount of methanol. Yield 4.0 g. This material is then dissolved in 100 ml. of methanol and treated with 4.0 g. of zinc dust at reflux for 15 minutes on the steam bath. No starting material is left at this point. The zinc is filtered off and the preparation taken to dryness. The solid is extracted with methanol and the extracts added to a 200 g. column of silica gel and eluted with 20, 50 ml. fractions of MEK, acetone, H₂O (72:20:8). Fraction 14 contains a few mgs. of crystals which are recrystallized from acetone-H₂O, m.p. 244°–245° dec. This material moves on TLC at about the same rate as the 5'-O-benzoyl CA, 35'-O-benzoyl and the 2'-O-benzoyl CA.

EXAMPLE 20

Preparation of 5'-O-2,4,6-triisopropylbenzenesulfonyl ara-cytidine

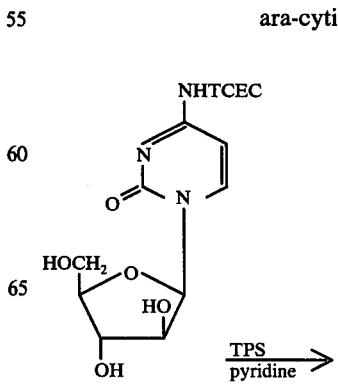

EXAMPLE 21

Preparation of 5'-O-isobutyryl ara-cytidine

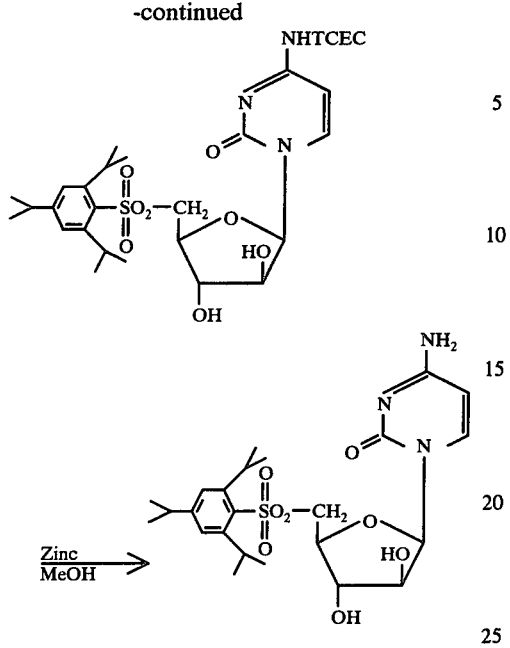

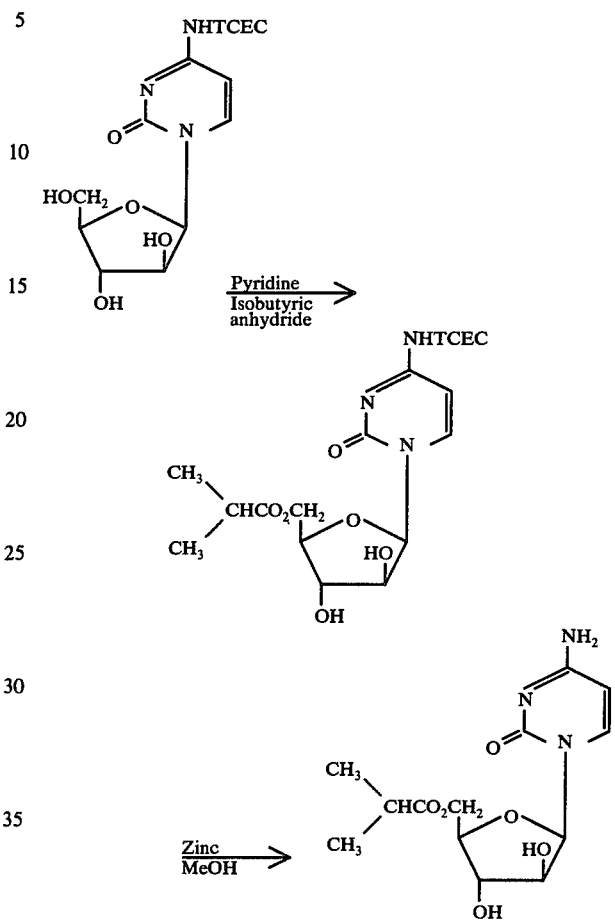

A 4.18 g. (10 millimoles) sample of N$^4$-trichloroethoxycarbonyl ara-cytidine is dissolved in 50 ml. of freshly distilled anhydrous pyridine. The solution is treated dropwise with 4.54 g. (15 millimoles) of 2,4,6-triisopropylbenzenesulfonyl chloride dissolved in 10 ml. of pyridine. The reaction mixture is allowed to stir at room temperature over the weekend then poured into 60 ml. of water and taken to dryness at 50°. This crude gum is then dissolved in 50 ml. of methanol, 5 g. of zinc dust added and the reaction mixture heated to boiling for one-half hour on the steam bath. TLC shows no starting material left. The preparation is filtered free of zinc and taken to dryness on the rotary evaporator. The crude gum is then absorbed onto a 200 g. column of silica gel and eluted with 20, 100 ml. fractions of MEK, acetone and H$_2$O. Fractions 7–20 all show one spot by TLC moving a little slower than the starting material and appearing to be the desired product. A 1 l. strip fraction of methanol is taken and also contains some material that was one spot moving with the fractions 7–10. Fractions 7–20 and the 1 l. methanol strip are combined, taken to dryness and crystallized once from methanol-water, then again from methanol. Yield 1.175 g., m.p. 188.5°–89.5° sl. dec. Another m.p. on the same sample does not melt until 228° and it dec. Recrystallized, from methanol a sample for analysis, m.p. 228° dec.

Anal. Calcd. for C$_{24}$H$_{35}$O$_7$N$_3$S: C, 56.56; H, 6.92; N, 8.25; S, 6.29. Found: C, 56.58; H, 6.94; N, 8.23; S, 6.08.

Ultraviolet Spectrum [$\lambda_{max}^{EtOH}$ ($\epsilon \times 10^{-3}$)]: 228 (17.85); 274 (10.60); 283 sl sh (8.60).

Infrared Spectrum [$\gamma_{cm-1}^{mull}$]: 3350, 3280, 3220, 3160 sh. 1665, 1640, 1615, 1575 sh. 1530, 1495, 1350, 1290, 1180, 1100, 1090, 1010, 980, 960 and 790.

NMR and the infrared spectrum are proper for the sulfonate.

A 8.36 g. (20 millimoles) sample of N$^4$-trichloroethoxycarbonyl ara-cytidine is dissolved in 10 ml. of freshly distilled anhydrous pyridine. The solution is treated with 3.5 g. (about 22 millimoles) of isobutyric anhydride dropwise at room temperature with stirring. The reaction mixture is allowed to stir at room temperature overnight. A TLC is run on the crude reaction in the morning. 25 ml. of water is added to the preparation and the preparation is taken to dryness at 50°. The glassy residue is then absorbed onto a 200 g. column of silica gel and eluted with 10, 100 ml. fractions of cyclohexane, ethyl acetate, 95% EtOH (5:3:1). TLC's are run on the first of the fractions. Fractions 5 and 6 are combined on the basis of the TLC results and recrystallized from methanol. Yield 2.0 g., m.p. 255° dec. One spot by TLC. This 2.0 g. of material is then dissolved in 50 ml. of methanol and treated with 2.0 g. of zinc dust at reflux for 10 minutes on the steam bath. TLC shows no starting material left. The zinc is filtered off and the methanol removed at 50° on the rotary evaporator. The clear glassy residue is then absorbed onto a 200 g. column of silica gel made up with cyclohexane, ethyl acetate, 95% EtOH (5:3:1). The column is eluted with 1 l. of the same solvent. Only a small amount of oil is eluted. The column is then eluted with 12, 100 ml. fractions of methyl ethyl ketone, acetone, H$_2$O (72:20:8). TLC's are run on fractions 5 through 9. On the basis of the results fractions 7, 8 and 9 are combined and recrystallized from water. Yield, 990 mg., m.p. 179°–184°. Recrystallized from water once for analysis, a sample has m.p. 206°–208°. (Heating rate about 3° per minute. Melting point varies.) If put in bath at 180°, sample melts immediately. If heating rate was 15°–20° per minute, m.p. 212–214°.

Anal. Calcd. for $C_{13}H_{19}O_6N_3 \cdot 1/2\ H_2O$: C, 48.44; H, 6.25; N, 13.04 Found: C, 48.62; H, 5.98; N, 13.33

Ultraviolet Spectrum $[\lambda_{max}^{EtOH}(\epsilon \times 10^{-3})]$: 233 sl sh (7.60); 273 (8.70).

Infrared Spectrum $[\gamma_{cm^{-1}}^{mull}]$: 3400, 3340, 328 sh, 3210, 3120 sh, 1740, 1715, 1655, 1640, 1625, 1535, 1490, 1285, 1205, 1165, 1110, 1095, 1050, 815, and 780.

EXAMPLE 22

Preparation of 5'-O-3,4,5-trimethoxybenzoyl ara-cytidine

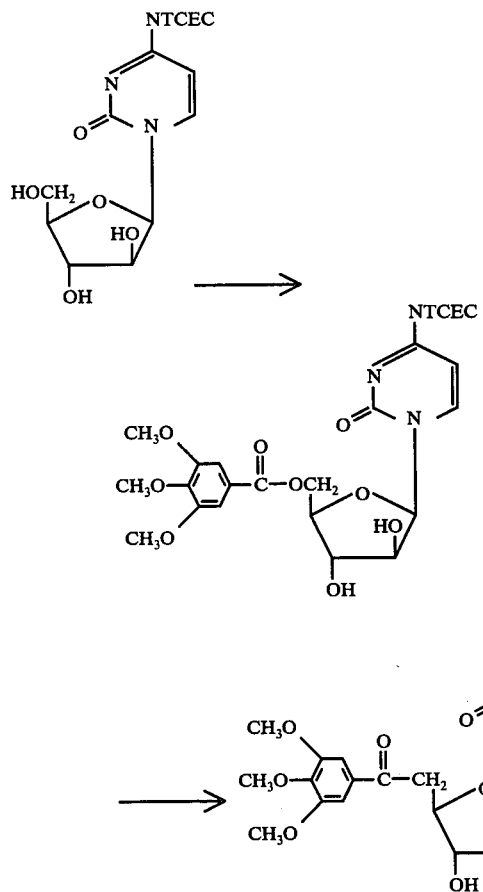

A 8.36 gram (20 millimole) sample of $N^4$-trichloroethoxycarbonyl ara-cytidine is dissolved in 100 ml. of freshly distilled anhydrous pyridine. The solution is treated with stirring and at room temperature with 4.85 g. (about 22 millimole) of 3,4,5-trimethoxybenzoyl chloride. Reaction is allowed to stir overnight at room temperature. A TLC was run in the morning, in the system silica gel, cyclohexane, ethyl acetate, 95% EtOH. The solution still shows starting material left. The reaction mixture is heated to 50° in an oil bath overnight. TLC plate shows no starting material in the crude mixture. Compound streaks and is hard to recognize. A white solid that precipitates out of the solution is spotted also. This material does not move from the origin. The reaction mixture is poured into 60 ml. of water and taken to dryness on the rotary evaporator. The gum is absorbed onto a 200 g. column of silica gel and eluted with 15, 100 ml. fractions of cyclohexane, ethyl acetate, 95% EtOH. Column is made up with this solvent also. On the basis of TLC results, fractions 4–9 are combined in methylene chloride, washed once with saturated bicarbonate once with water, dried through sodium sulfate and taken to dryness. This removes all the slower moving material which is the trimethoxy benzoyl acid by TLC. The residue is dissolved in 100 ml. methanol and 3 g. zinc dust were added. This mixture was heated at the reflux temperature for 10–15 mins. and then cooled. The cooled solution was filtered to remove zinc dust, and the methanol was removed by evaporation at 50° C. The residue thus obtained (8.17 g.) was dissolved in methylene chloride and absorbed onto a 200 g. column of silica gel made up with MEK, acetone, $H_2O$ (72:20:8) and eluted with 12, 100 ml. fractions of the same solvent. Fractions 6, 7, 8 and 9 are spotted on a TLC plate and run in the same solvent. Based on the TLC results fractions 7, 8 and 9 are combined and recrystallized from methanol. Yield 2.410 g., m.p. 143°–145°. Recrystallized from methanol, a sample for analysis shows, m.p. 137°–139°.

Anal. Calcd. for $C_{19}H_{23}O_9N_3 \cdot 1\ H_2O$: C, 50.11; H, 5.53; N, 9.23 Found: C, 50.50; H, 5.41; N, 9.15.

Ultraviolet Spectrum $[\lambda_{max}^{EtOH}(\epsilon \times 10^{-3})]$: 214 (40.30); 269 (17.75); 305 sl sh (2.55).

Infrared Spectrum $[\gamma_{cm^{-1}}^{mull}]$: 3420, 3320, 3260, 3220, 1715, 1645, 1600, 1520, 1500, 1340, 1280, 1225, 1125, 1095, 1075, 1065, 1030, 995, 860, and 805.

Both ultraviolet spectrum and infrared spectrum are proper for the proposed structure.

EXAMPLE 23

Preparation of 5'-O-2,6-dimethylbenzoyl ara-cytidine

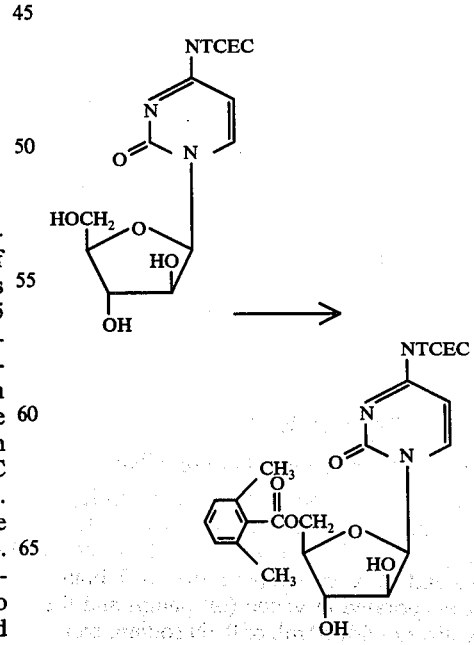

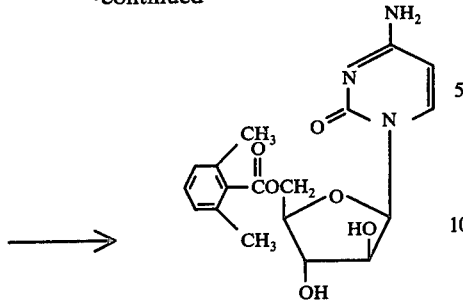

A 8.36 g. (20 millimole) sample of N⁴-trichloroethoxycarbonyl ara-cytidine is dissolved in 100 ml. of freshly distilled anhydrous pyridine. The solution is treated at room temperature with 3.70 g. (about 22 millimole) of 2,6-dimethylbenzoic chloride. The reaction mixture is stirred overnight. The chloride is dissolved in 10 ml. of $CH_2Cl_2$ and added dropwise. TLC in the morning shows some starting material left. Another 3.70 g. in 10 ml. of $CH_2Cl_2$ is added dropwise and the preparation allowed to go overnight at room temperature. In the morning TLC shows almost no starting material left. 50 ml. of water are added and the preparation taken to dryness at 50° on a rotary evaporator. The residue is dissolved in 200 ml. of $CH_2Cl_2$ and extracted twice with 100 ml. each of saturated bicarbonate. The $CH_2Cl_2$ solution is washed once with 200 ml. of $H_2O$ and dried through sodium sulfate, then taken to dryness. The gum is then absorbed onto a 200 g. column of silica gel made up with cyclohexane, ethyl acetate, 95% EtOH. The column is eluted with 20, 100 ml. fractions of the same solvent. TLC's are run on fractions 7–15. Based on the TLC results, fractions 7–12 are combined and recrystallized from methanol. Yield 3.0 g. This material has one spot by TLC and moves the same on the plate as 2,4,6-trimethylbenzoyl N⁴-trichloroethoxycarbonyl ara-cytidine. This 3 g. of material is dissolved in 100 ml. of methanol, 3 g. of zinc dust added and the preparation heated to reflux for 15 minutes on the steam bath. At this time TLC shows no starting material left. The zinc is filtered off and the methanol removed in the evaporator. The clear glassy residue is then absorbed onto a 200 g. column of silica gel made up with MEK, acetone, $H_2O$ (72:20:8) and eluted with 10, 100 ml. fractions of the same solvent. TLC's are run on fractions 3, 4, 5 and 7. Fractions 4–9 are combined and recrystallized from methanol. The yield is 1.24 g. m.p. 238°–240° dec. A sample is recrystallized once from methanol for analysis, m.p. 238°–240° dec.

Anal. Calcd. for $C_{18}H_{21}O_6N_3 \cdot 1/2\ H_2O$: C, 56.24; H, 5.77; N, 10.93. Found: C, 56.31; H, 6.03; N, 11.17

Ultraviolet Spectrum $[\lambda_{max}^{EtOH}(\epsilon \times 10^{-3})]$: 233 sl sh (10.25); 273 (9.55).

Infrared Spectrum $[\epsilon_{cm^{-1}}{}^{mull}]$: 3500 sh. 3400, 3340, 3280 w, 3220, 1740 sh, 1715, 1655, 1635, 1615, 1530, 1485, 1785, 1270, 1245, 1110; 1095, 1070, 1050, 815 and 710.

EXAMPLE 24

Preparation of 5'-O-palmityl ara-cytidine

Ara-cytidine hydrochloride (2.80 g., 0.01 mole) is dissolved in 25 ml. dimethylformamide and 3.05 g. (0.011 mole) of palmityl chloride is added. The solution is allowed to stand at room temperature for 7 hours. The solvent is evaporated in vacuo (oil pump) and the resultant oil is stirred with 70 ml. of 0.3N sodium bicarbonate. The resultant solid is collected on a filter, washed several times with water, pressed dry, and then washed three times with 25 ml. ethyl acetate and air dried. Yield, 2.52 g. (52%), m.p. 135°–145°. Thin layer chromatography showed a single ultraviolet-absorbing spot in several solvent systems. A sample is recrystallized once from methanol (82% recovery) for analysis, m.p. 145°–148°.

Anal. Calcd. for $C_{25}H_{43}N_3O_6$: C, 62.34; H, 9.00; N, 8.72. Found: C, 62.65; H, 9.29; N, 8.75

Infrared and ultraviolet absorption curves are identical to that of an authentic sample, and the material is chromatographically identical to the authentic sample in several solvent systems.

EXAMPLE 25

Preparation of 5'-pivaloyl ara-cytidine

Ara-cytidine hydrochloride (3.5 g., 0.01 mole on the basis of 20.5% solvent of crystallization), is suspended in 25 ml. of dimethylacetamide and 1.3 g. (10% excess) of pivaloyl chloride is added. The mixture is stirred at room temperature. As the material reacts it slowly dissolves. After stirring overnight, the mixture is clear. The solution is concentrated to a low-volume in vacuo (oil pump) and the residual oil is stirred with 100 ml. ethyl acetate-ether (1:1). This treatment is repeated twice more, decanting and centrifuging. The semi-solid is then triturated with 20 ml. of N $NaHCO_3$, filtered, and washed several times on the filter with water. The white crystalline solid is dried in an air stream. Yield 2.24 g. (66%), m.p. 252°–258° dec. TLC (EtOAC-DMF-$H_2O$, 75:15:5) shows that the material consist of a single spot*, Rf = 0.38. About 1 g. of this material is recrystallized from 15 ml. methanol. Recovery 0.4 g., m.p. 261°–262° dec. The remainder of the material (1.24 g.) is stirred with hot butanol. It changes crystalline form and becomes sparingly soluble in the butanol. A total of 25 ml. of hot butanol is used, but much remains insoluble. Recovery 1.04 g., m.p. 259°–260° dec. The mother liquors are combined, evaporated to dryness, and the residue is recrystallized from methanol. Recovery 0.36 g., m.p. 254°–256° dec.

*Rf identical to that of an authentic sample

EXAMPLE 26

Preparation of 5'-octanoyl ara-cytidine

Ara-cytidine hydrochloride (5.6 g., 0.02 mole) is dissolved in 50 ml. dimethylformamide and 3.6 g. (0.022 mole) of octanoyl chloride is added. The clear solution is allowed to stand over the weekend.

TLC shows that a good yield of the product (Rf = 0.38 run with an authentic sample as standard) is obtained, with a trace of a component of Rf = 0.95, small amounts of other products of Rf's = 0.70, 0.52, 0.24, and material of low Rf trailing to the origin. The solvent is evaporated with vacuum and the oil is stirred with about 100 ml. ether three times. The semi-solid is then thoroughly stirred with 40 ml. N $NaHCO_3$, the resultant solid is collected and washed with $H_2O$ until neutral. The solid is air-dried. Weight 4.89 g. TLC (as above) shows that the product at this stage has a small amount of materials of Rf's = 0.70 and 0.52 and a trace of material trailing behind the product. The product is crystallized from 60 ml. hot ethyl acetate as needles. Recovery 4.07 g. (55%), m.p. 158°–161°.

EXAMPLE 27

Preparation of 5'-cyclohexylcarbonyl ara-cytidine

Ara-cytidine hydrochloride (20% by weight of solvent; 17.5 g., 0.05 mole) is dissolved in 125 ml. dimethylformamide and 8.06 g. (10% excess) of cyclohexanecarboxylic acid chloride is added. The clear solution is allowed to stand at room temperature overnight.

The solvent is evaporated in vacuo and the oil is stirred several times with ether. The oil is then thoroughly triturated with 100 ml. N sodium bicarbonate. The solid is filtered, washed with water and air dried. The material is crystallized from 100 ml. ethyl acetate. The material dissolves readily in warm ethyl acetate and then crystallizes out in a form that will not redissolve in this solvent. The crystalline material is collected, washed with ethyl acetate, ether and dried. Weight 5.58 g., m.p. 232° dec. The mother liquor is evaporated to dryness and the crystalline residue is triturated with hot ethyl acetate, cooled and collected as above. Weight 3.86 g., m.p. 227°–229° dec. Total yield 9.44 g. (53%). The Rf is identical to that of an authentic sample.

EXAMPLE 28

Preparation of 5'-acetyl-ara-cytidine

Ara-cytidine hydrochloride dimethylformamide solvate (17.5 g., 0.05 mole) is dissolved in 125 ml. dimethylformamide and 4.32 g. (10% excess) of acetyl chloride is added. The clear solution is allowed to stand overnight at room temperature.

The solvent is evaporated in vacuo, and the resulent oil is stirred several times with ether. The residual oil is dissolved in water, the pH is adjusted to 1.5, and the solution is extracted three times with equal volumes of ethyl acetate. The pH of the aqueous solution is adjusted to 7, and the solvent is evaporated in vacuo. The residual oil is dissolved in ethanol and sodium chloride is removed by filtration. The solvent is evaporated in vacuo to leave an oil weighing 16.5 g.

About 13 g. of this product is purified by chromatography over silica gel (Merck-Darmstadt, 0.05–0.2 mm) using the solvent system methylethylketone-acetone-water (72:20:8). About 800 g. of adsorbent for a column 56 mm in diameter is used. The material is dissolved in a small volume of water for adsorption on the column, and then elution with the solvent is begun. The volume of each fraction is 100 ml., and the elution of the material is followed by TLC. The 5'-acetyl ara-cytidine is eluted in fractions 33–51, which is combined and evaporated in vacuo to leave a crystalline residue weighing 7.0 g. The product is recrystallized from 60 ml. 1-butanol, recovery 4.05 g., m.p. 184°–185°. TLC in several solvent systems shows that the material is chromatographically identical to an authentic sample of 5'-acetyl ara-cytidine. A small amount of additional product is recovered from the mother liquor above to give a total yield of purified product of 38%.

EXAMPLE 29

Preparation of 5'-adamantoyl ara-cytidine

Ara-cytidine hydrochloride (63 g., 0.225 mole) is suspended in 1100 ml. of dimethylacetamide. About 51 g. (10% excess) of 1-adamantanecarboxylic acid chloride is added and the mixture is stirred overnight at room temperature. The mixture is filtered to remove about 4.8 g. of solid. TLC of the filtrate shows a considerable amount of unreacted cytosine arabinoside. An additional 32 g. (0.16 mole) of 1-adamantanecarboxylic acid chloride is added and the reaction is allowed to proceed for an additional 24 hours. The solution is concentrated in vacuo to a low volume and the oil is triturated three times with 500 ml. of ethyl acetate-ether (1:1). The oil is thoroughly triturated with 650 m. N $NaHCO_3$, the resultant crystalline solid is collected by filtration and washed several times with water. The filter cake is pressed dry and the solid is washed twice with ethyl acetate and then with ether, and dried. Yield, 63 g. (69%), m.p 282° dec. Recrystallization from 400 ml. dimethylacetamide-1600 ml. ethyl acetate gives 61.1 g., m.p. 291° dec. TLC in several solvent systems, and comparative melting point determinations show that the product is identical to an authentic sample of 5'-adamantoyl aracytidine.

EXAMPLE 30

Preparation of 5'-O-L-trans-3-[n-propyl]-hygric acid ester of ara-cytidine

L-trans-3-[n-propyl]-hygric acid hydrochloride is heated to reflux in excess thionyl chloride until the acid is completely dissolved. The excess thionyl chloride is then removed by distillation under reduced pressure. The residue is taken to dryness three times with 5 volumes of dry benzene. The residue is then dissolved in a minimum amount of dry dimethylacetamide and added to a solution of ara-cytidine hydrochloride in the same solvent and stirred at room temperature overnight. The 5'-ester is then isolated as described in Example 22.

EXAMPLE 31

Preparation of 5'-lauroyl-ara-cytidine

Ara-cytidine hydrochloride (5.0 g., 0.018 mole) is dissolved in 45 ml. dimethylformamide and 4.33 g. (0.02 mole) of lauroyl chloride is added dropwise. The reaction mixture is stirred overnight at room temperature. The solvent is evaporated at reduced pressure and the resulting gum triturated with 1N sodium bicarbonate. The resulting precipitate is filtered and dissolved in a minimum volume of acetone and the solution filtered. The solution is allowed to cool to room temperature and the product crystallizes. After all apparent crystallization has occurred, it is stored in the freezer overnight. Filtration provides 4.6 g. (60%) of a white solid, m.p. 153°–155° C. TLC (MEK*:acetone:$H_2O$, 60:20:15) shows one zone, Rf=0.57.

*methyl ethyl ketone

Analysis: Calc'd. for $C_{21}H_{35}N_3O_6 \cdot \frac{1}{2}H_2O$: C, 58.04; H, 8.35; N, 9.67.

Found: C, 58.10; H, 8.59; N, 9.50.

Infrared Spectrum [$\gamma_{cm^{-1}}{}^{mull}$]: 3400, 3340, 3230, 1735, 1635, 1600, 1535, 1485, 1280, 1165, 1110 and 1040.

EXAMPLE 32

Preparation of 5'-O-lauroyl-ara-cytidine hydrochloride

Following the procedure of Example 7, 5'-O-lauroyl-ara-cytidine hydrochloride is prepared by substituting 5'-O-lauroyl-ara-cytidine for 5'-palmityl cytosine arabinoside.

EXAMPLE 33

Tablets for Oral Administration

1000 Scored tablets for oral use, each containing 500 mg. of 5'-O-palmityl ara-cytidine, are prepared from the following types and amounts of ingredients:

| | | |
|---|---|---|
| 5'-O-palmityl ara-cytidine | 500 | gm. |
| Starch, U.S.P. | 35 | gm. |
| Talc, U.S.P. | 25 | gm. |
| Calcium stearate | 3.5 | gm. |

The powdered 5'-O-palmityl ara-cytidine is granulated with a 4% w./v. aqueous solution of methylcellulose U.S.P. To the dried granules is added a mixture of the remainder of the ingredients and the final mixture is compressed into tablets of proper weight.

Satisfactory clinical response is obtained in adults with acute leukemia with 1 tablet 3 times a day.

Using the procedure above, tablets are similarly prepared containing 5'-O-palmityl ara-cytidine in 3 mg. and 1000 mg. amounts by substituting 3 gm. and 1000 gm. of 5'-O-palmityl ara-cytidine for the 500 gm. used above.

EXAMPLE 34

Injectable Dispersion

A sterile aqueous dispersion suitable for intramuscular use, and containing 250 mg. of 5'-O-palmityl ara-cytidine hydrochloride in each ml., is prepared from the following ingredients:

| | | |
|---|---|---|
| 5'-O-palmityl ara-cytidine hydrochloride | 250 | gm. |
| Water for injection, q.s. | 1,000 | gm. |

A daily dose of 1 ml. provides a satisfactory clinical response.

EXAMPLE 35

Injectable Preparation

A sterile aqueous preparation suitable for intramuscular injection and containing 10 mg. of 5'-O-palmityl ara-cytidine in each 2 ml. is prepared from the following ingredients:

| | | |
|---|---|---|
| 5'-O-palmityl ara-cytidine | 5 | gm. |
| Polyethylene glycol, 4000 U.S.P. | 30 | gm. |
| Sodium chloride, U.S.P. | 9 | gm. |
| Preservative, q.s. | | |
| Water for injection, q.s. | 1,000 | ml. |

EXAMPLE 36

Injectable Preparation

A sterile preparation suitable for intramuscular injection and containing in each milliliter 100 mg. of 5'-O-palmityl ara-cytidine is prepared from the following types and amounts of materials:

| | | |
|---|---|---|
| 5'-O-palmityl ara-cytidine | 100 | gm. |
| Aluminum monostearate-peanut oil gel, q.s. to | 1,000 | gm. |

A mixture of 2 parts aluminum monostearate and 98 parts of peanut oil is slowly heated with stirring to a temperature of 100° C. The temperature is maintained at this level for 1 hour when gelling is complete and is then raised to 150° C. and maintained at this temperature for 1 hour. The gel is then cooled and 100 grams of sterile, powdered 5'-O-palmityl ara-cytidine is incorporated aseptically with stirring and the total volume made up to 1000 ml. with additional gel and further stirring.

EXAMPLE 37

Sterile Powder for Reconstitution

Sterile vials each containing 50 mg. of 5'-O-palmityl ara-cytidine hydrochloride are prepared by first sterilizing 50 gm. of the 5'-O-palmityl ara-cytidine by treatment with ethylene oxide and thereafter filling 50 mg. into each of 1000 sterile vials. At the time of use, the contents of a vial are reconstituted with q.s. water for injection to provide a sterile preparation for injection administration.

EXAMPLE 38

Sterile Preparation 24,000 Ml. of sterile preparation are prepared as follows:

| Each ml.: | Total |
|---|---|
| 57.5 mg. 5'-O-palmityl ara-cytidine hydrochloride | 1380 gm. |
| 5 mg. sodium citrate | 120 gm. |
| 9.45 mg. benzyl alcohol | 227 gm. |
| 2.3 mg. sodium bisulfite | 55.2 gm. |
| Sodium hydroxide (50% aqueous solution), q.s. | |
| Water for injection, q.s. ad | 24,000 ml. |

Directions: Dissolve the 5'-O-palmityl ara-cytidine hydrochloride, sodium citrate and benzyl alcohol in 2,000 ml. water. Add the sodium bisulfite and adjust the pH 7.0 with the alkali.

EXAMPLE 39

Following the procedure of the preceding Examples 33, 35, and 36, compositions are prepared substituting equivalent amounts of the pharmaceutically acceptable acid addition salts of 5'-O-palmityl ara-cytidine for the free base of the examples.

EXAMPLE 40

Following the procedure of the preceding Examples 34, 37 and 38, compositions are prepared substituting equivalent amounts of the free base of 5'-O-palmityl ara-cytidine hydrochloride for the pharmaceutically acceptable acid addition salt of the examples.

EXAMPLE 41

Following the procedure of the preceding Examples 33, 35, and 36, compositions are prepared substituting equivalent amounts of the other ester compounds of the subject invention or the pharmaceutically acceptable acid addition salts of each for 5'-O-palmityl ara-cytidine to provide similar therapeutic properties.

EXAMPLE 42

Following the procedure of the preceding Examples 34, 37, and 38, compositions are prepared substituting equivalent amounts of the free base of the other ester compounds of the subject invention or the pharmaceutically acceptable acid addition salts of each for 5'-O-palmityl ara-cytidine hydrochloride to provide similar therapeutic properties.

EXAMPLE 43

Preparation of 5'-O-(p-anisoyl) ara-cytidine hydrochloride

Following the procedure of Example 7, 5'-O-(p-anisoyl) ara-cytidine hydrochloride is prepared by substituting 5'-O-(p-anisoyl) ara-cytidine for 5'-palmityl cytosine arabinoside.

We claim:

1. A compound having the following structural formula:

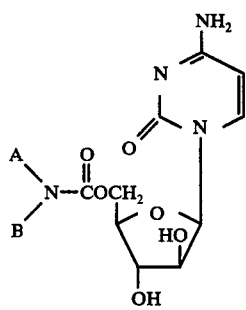

in which A and B are the same or different radicals selected from the group consisting of H, aliphatic of from 1 to 10 carbon atoms, monocyclic aliphatic of from 4 to 10 carbon atoms, and aromatic of from 6 to 10 carbon atoms, and further in which A and B together can make up an aliphatic chain of from 3 to 6 carbon atoms, or the pharmaceutically acceptable acid addition salts thereof.

2. A compound having the following structural formula:

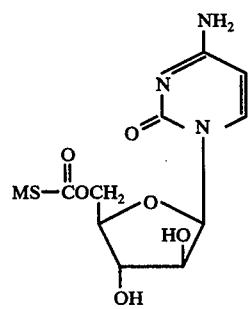

in which M is a radical selected from the group consisting of aliphatic of from 1 to 10 carbon atoms, monocyclic aliphatic of from 4 to 10 carbon atoms, aromatic of from 6 to 10 carbon atoms, and aralkyl of from 7 to 12 carbon atoms, or the pharmaceutically acceptable acid addition salts thereof.

3. A compound having the following structural formula:

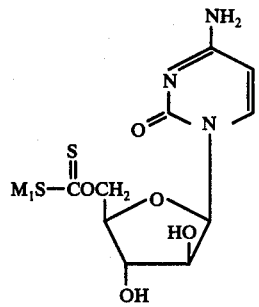

wherein $M_1$ is a radical selected from the group consisting of aliphatic of from 1 to 10 carbon atoms, aromatic of from 6 to 10 carbon atoms, and araliphatic of from 7 to 12 carbon atoms, or the pharmaceutically acceptable acid addition salts thereof.

4. A compound having the following structural formula:

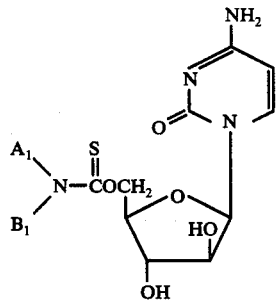

wherein $A_1$ and $B_1$ are the same or different radicals selected from the group consisting of H, alkyl of from 1 to 7 carbon atoms, and aromatic of from 6 to 10 carbon atoms, or the pharmaceutically acceptable acid addition salts thereof.

5. A compound of the following structural formula:

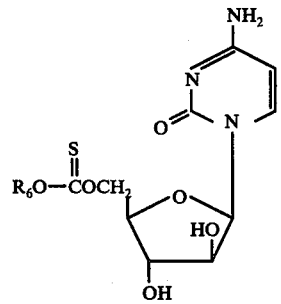

wherein $R_6$ is a radical selected from the group consisting of aliphatic of from 1 to 20 carbon atoms, aromatic of from 6 to 10 carbon atoms, and araliphatic of from 7 to 12 carbon atoms, or the pharmaceutically acceptable acid addition salts thereof.

* * * * *

UNITED STATES PATENT AND TRADEMARK OFFICE
CERTIFICATE OF CORRECTION    Page 1 of 4

PATENT NO. : 4,096,324
DATED      : June 20, 1978
INVENTOR(S) : Robert C. Kelly and William J. Wechter It is certified that error appears in the above—identified patent and that said Letters Patent is hereby corrected as shown below:

Front page, line 20: "inmunosuppressive" should read -- immunosuppressive --.
Front page, line 20: "derivaritives" should read -- derivatives --.
Column 3, line 13:   " (about 2 moles) ⟶ " should read -- (about 2 moles) ⟶ pyridine --.

Column 3, line 46:    should read -- .

Column 5, line 23:   " ∕ \;sb,15 0 " should read -- ∕O\ --.

Column 5, line 68: "Oh" should read -- OH --.
Column 6, line 19: "wich" should read -- which --.
Column 8, line 10: "HO" should read -- HO
                                          |   --.

Column 8, lines 60-61:  "O      should read --  S
                         ‖                      ‖  --.
                         C                      C Column 10, line 43: "3,338,832" should read -- 3,338,882 --.
Column 10, line 49: "cytidane." should read -- cytidine. --.
Column 11-12, Table I, No. 10: 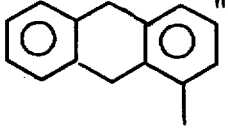 should read -- 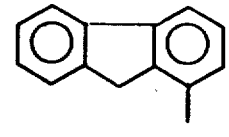 --.

Column 13, Table I, No. 14: " " should read -- --.

UNITED STATES PATENT AND TRADEMARK OFFICE
CERTIFICATE OF CORRECTION

PATENT NO. : 4,096,324
DATED : June 20, 1978
INVENTOR(S) : Robert C. Kelly and William G. Wechter It is certified that error appears in the above—identified patent and that said Letters Patent is hereby corrected as shown below:

Column 13, Table I, No. 18: " CH$_3$O 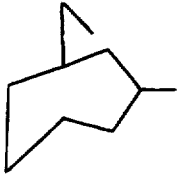 " should read -- CH$_3$O 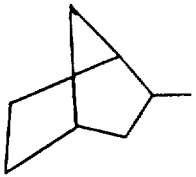 --.

Column 13, Table I, No. 20: " CH$_3$O  " should read -- CH$_3$O 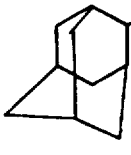 --.

Column 13, Table I, No. 21: "  " should read --  --.

Column 14, Table I, No. 23: "norbornye-" should read -- norbornyl- --.

Column 13, Table I, No. 24: "  " should read -- --.

Column 15, Table I, No. 31: " " should read -- --.

Column 16, Table I, No. 40: "furoyl)ara-furoyl)ara-cytidine" should read -- furoyl)ara-cytidine --.

Column 18, line 65: "O
                     |
                     C"  should read -- O
                                        ‖
                                        C --.

Column 19, Table II, 7th formula under column B: "◯" should read -- --.

UNITED STATES PATENT AND TRADEMARK OFFICE
CERTIFICATE OF CORRECTION  Page 3 of 4

PATENT NO. : 4,096,324
DATED : June 20, 1978
INVENTOR(S) : Robert C. Kelly and William G. Wechter It is certified that error appears in the above—identified patent and that said Letters Patent is hereby corrected as shown below:

Column 19, Table II, 8th formula under Column A: "        " should read

Column 19, line 66: "atpms" should read -- atoms --.
Column 20, line 58: "$CDCl_2$" should read -- $COCl_2$ --.

Column 21, line 5: "        " should read -- 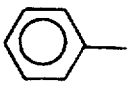 --.

Column 22, line 58: "55'-oxygen" should read -- 5'-oxygen --.
Column 23, lines 47-48: "phosphorchloridates" should read -- phosphochloridates --.
Column 23, Table VIII, last line: "5'-" should read -- (5'- --.
Column 25, line 22: "acryl" should read -- acyl --.
Column 25, line 68: "resulting" should read -- resultant --.
Column 27, line 17: "$CCL_3$" should read -- $CCl_3$ --.
Column 28, line 66: "($\gamma$ cm-$^1$mull)" should read -- ($\gamma_{cm-1}^{mull}$)

Column 33, line 54: "7..97;" should read -- 7.97; --.
Column 35, line 8: "115°-117.5°." should read -- 115-117.5. --.
Column 35, line 12: "[$\gamma_{max}^{etOH}$" should read -- [$\gamma_{max}^{EtOH}$ --.
Column 36, line 43: "5'0-" should read -- 5'-O- --.
Column 36, line 44: "5'0-" should read -- 5'-O- --.
Column 36, line 45: "5'0-" should read -- 5'-O- --.
Column 36, line 48: "5'0-" should read -- 5'-O- --.
Column 36, line 49: "5'0-" should read -- 5'-O- --.
Column 36, line 58: "dri" should read -- dry --.
Column 36, line 66: "1 N" should read -- .1 N --.
Column 37, line 33: "aded" should read -- added --.
Column 38, line 41: "Th" should read -- The --.

UNITED STATES PATENT AND TRADEMARK OFFICE
CERTIFICATE OF CORRECTION

PATENT NO. : 4,096,324
DATED : June 20, 1978
INVENTOR(S) : Robert C. Kelly and William J. Wechter It is certified that error appears in the above—identified patent and that said Letters Patent is hereby corrected as shown below:

Column 38, line 50: "TLC." should read -- TLC, --.
Column 38, line 64: "mull$_{)]}$." should read -- mull$_]$: --.
Column 39, line 52: "rotry" should read -- rotary --.
Column 41, line 14: "acetone. $H_2O$" should read -- acetone, $H_2O$ --.
Column 46, line 11: "NeOH" should read -- MeOH --.
Column 46, line 49: "35'-" should read -- 3'- --.
Column 47, line 65: "sh." should read -- sh, --.
Column 47, line 65: "sh." should read -- sh, --.
Column 49, line 47: "$CH_2$" should read -- $OCH_2$ --.
Column 51, line 56: "[ε" should read -- [γ --.
Column 51, line 56: "sh." should read -- sh, --.
Column 53, line 33: "resulent" should read -- resultant --.
Column 54, line 7: "m." should read -- ml. --.
Column 58, line 47: "$R_6O-COCH_2$" should read -- $R_6O-C-OCH_2$ --.

Signed and Sealed this

Sixteenth Day of November 1982

[SEAL]

Attest:

GERALD J. MOSSINGHOFF

Attesting Officer

Commissioner of Patents and Trademarks